United States Patent [19]
Wetterlin et al.

[11] 4,011,258
[45] Mar. 8, 1977

[54] ORALLY ACTIVE BRONCHOSPASMOLYTIC COMPOUNDS

[75] Inventors: Kjell Ingvar Leopold Wetterlin, Sandby; Leif Ake Svensson, Lund, both of Sweden

[73] Assignee: Aktiebolaget Draco, Lund, Sweden

[22] Filed: July 7, 1975

[21] Appl. No.: 593,424

Related U.S. Application Data

[60] Division of Ser. No. 372,497, June 21, 1973, Pat. No. 3,937,838, which is a continuation-in-part of Ser. Nos. 55,791, July 17, 1970, and Ser. No. 55,676, July 17, 1970, said Ser. No. 55,791, said Ser. No. 55,676, each is a continuation-in-part of Ser. No. 676,288, Oct. 18, 1967, abandoned.

[52] U.S. Cl. .................. 260/479 R; 260/570.6
[51] Int. Cl.² ................ C07C 93/26; C07C 91/34
[58] Field of Search .............. 260/479 R, 570.6

[56] References Cited
UNITED STATES PATENTS 3,180,887  4/1965  Zolss et al. .................. 260/479

OTHER PUBLICATIONS

Moed et al., Rec. Trav. Chim. Pay Bus. 71, 933 (1952).

Primary Examiner—Robert Gerstl
Attorney, Agent, or Firm—Brumbaugh, Graves, Donohue & Raymond

[57] ABSTRACT

Novel compounds are disclosed having useful activity as bronchodilators of improved longevity of action and reduced incidence of side effects. These compounds are described by the formula:

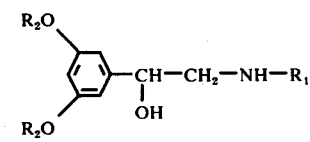

wherein $R_1$ is a member of the class consisting of tertiary butyl and cyclobutyl, and $R_2$ is a hydrogen or 2 to 5 carbon atom acyl radical, and pharmaceutically acceptable salts thereof. The activity of these compounds is compared to previously known bronchodilators such as 1-(3', 5'-dihydroxyphenyl)-2-(isopropylamino)-ethanol, having the common name orciprenaline, and 1-(3', 4'-dihydroxyphenyl-2-isopropylamino-ethanol, having the common name isoprenaline.

3 Claims, 9 Drawing Figures

ORALLY ACTIVE BRONCHOSPASMOLYTIC COMPOUNDS

This is a division, of application Serial No. 372,497 filed 6-21-73 now U.S. Pat. No. 3,937,383 which is a continuation-in-part of our copending applications Serial Nos. 55,791 and 55,676, filed July 17, 1970, which in turn are respectively both continuations-in-part of application Serial No. 676,288, filed October 18, 1967, now abandoned.

The present invention relates to compounds effective in the treatment of reversible obstructive lung conditions of various genesis, particularly asthmatic conditions, the preparation of such compounds, compositions containing them, and the use for therapeutic purposes of such compounds. In particular, the present invention relates to certain 1-(3′, 5′-dihydroxyphenyl)-2-alkylamino ethanols and 1-(3′, 5′-diacyloxyphenyl)-2-alkylamino ethanols, which are bronchospasmolytically active and have unexpected specificity and longevity of action.

The new compounds of the present invention have the structural formulas

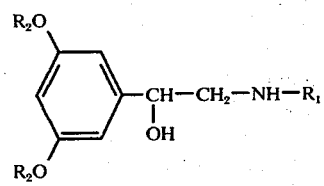

(I)

wherein $R_1$ is a member of the class consisting of tertiary butyl and cyclobutyl and $R_2$ is hydrogen or the acyl radical of a 2-5 carbon fatty acid. These compounds have long duration of activity as bronchospasmolytic agents and, surprisingly, cause only very weak side effects, especially effects on the cardiovascular system. The acyl derivatives are useful intermediates in the preparation of free hydroxy compounds, as well as being useful pharmacological agents in their own right.

The compounds of the present invention are also useful for the relaxation of the smooth muscles of the sphincter Oddi and the gall duct to relieve effects such as biliary colic, biliary dyskinesia and morphine spasms. The compounds of the present invention, when administered, cause a decrease of the pressure of the hepatic duct, but do not, in sphincter-active doses, have significant side effects on the heart or the intestinal system. This is a pronounced advantage relative to prior art compounds such as isoprenaline.

For years, sympathomimetic agents have been among the most important class of compounds in the treatment of asthma. Among the leading compounds used for this purpose is epinephrine, given by injection, for the relief of reversible obstructive lung conditions.

A great number of 1-(3′,4′-dihydroxyphenyl)-2-amino ethanols having bronchospasmolytic activity are known. Epinephrine and isoprenaline are the most important commerically of this class of compounds. However, compounds of this type with the two hydroxyl groups in the 3,4-position of the benzene ring are attacked in the patient by certain enzymes, i.e., catechol-O-methyltransferase (COMT), found, inter alia, in the liver. The COMT attack on these compounds inactivates them, and therefore their bronchodilator activity is typically of relatively short duration. Compounds having the two hydroxyl groups in the 3,5-position of the benzene ring are not attacked by COMT. However, rather few compounds of this last-mentioned type are known. The known compounds may be summarized by the general formula:

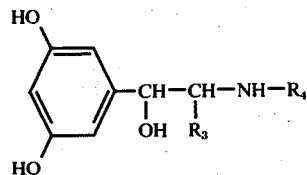

A compound of formula II wherein $R_3$ is hydrogen and $R_4$ is a methyl group has been described in German pat. No. 865,315. Compounds of formula II wherein $R_3$ is hydrogen and $R_4$ is 2-hexyl,2-heptyl,2-octyl or n-butyl have been described in Belgian pat. No. 635,889. Compounds wherein $R_3$ is hydrogen and $R_4$ is the group

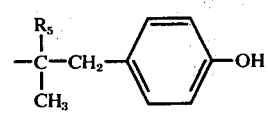

wherein $R_5$ is hydrogen or methyl, are described in Irish patent application No. 1167/63. Compounds wherein $R_3$ is hydrogen or methyl, and $R_4$ is isopropyl have been described in British pat. No. 920,623. These known compounds of formula I are bronchospasmolytically active of longer duration than those compounds containing the 3,4-dihydroxyphenyl groups, but they are generally found to cause an increase in the heart frequency, and this markedly reduces the therapeutic value of these substances.

These drugs are believed to act on the adrenergic receptor sites which are found widely distributed throughout the body and are classified, depending on the response elicited, into α- and β-receptors. Lands et al. in 1966 published data on the basis of which it was postulated that there are two different types of adrenergic β-receptors, designated respectively $\beta_1$ and $\beta_2$. The $\beta_1$-receptors are, among other places, located in the heart muscles while $\beta_2$-receptors are associated with the bronchial muscles. These findings of Lands et al. were based upon a rank order classification of a series of sympathomimetic amines of the general formula

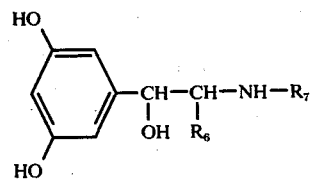

Lands′ study included testing of compounds in which $R_6$ was hydrogen and $R_7$ was isopropyl, tertiary butyl, secondary butyl, and cyclopentyl; and compounds of which $R_6$ was methyl or ethyl, and $R_7$ was isopropyl.

The use of the sympathomimetric amines in the treatment of reversible obstructive lung conditions is generally believed due to the ability of these compounds to stimulate the $\beta_2$-receptors in the bronchial system. The stimulation of the bronchial system by the sympathomimetic amines leads to relief of bronchoconstriction and improved lung mechanics as measured, for example, by various spirometric tests.

However, the sympathomimetric amines have side effects, which are mainly due to their stimulation of adrenergic receptors in organs other than the bronchial muscle. Thus, stimulation of the $\beta_2$- receptors in the bronchial muscle to achieve bronchodilation is commonly accompanied by simultaneous stimulation of the $\beta_1$-receptors in the myocardium. Such $\beta_1$- activity leads to tachycardia and an increase in the cardiac output. When $\alpha$-receptors are stimulated in addition, there is peripheral vasoconstriction and increased blood pressure. Thus, with the compounds previously available, bronchodilation was usually accompanied by undesirable and potentially dangerous cardiovascular stimulation. This is the most serious side effect of the sympathomimetic amines, especially in patients suffering from cardiovascular diseases such as coronary sclerosis, arrhythmias, and hypertension. In addition, the cardiovascular effects can increase the pulmonary blood volume. This may lead to an exaggeration of a disturbed ventilation-perfusion ratio in the lung, especially on overdosage, and to a worsening of hypoxemia, even though airway obstruction is diminished. The foregoing factors limited the dose of the sympathomimetic amines which could be used, and, indeed, represented potential risk in the use of such compounds.

Despite the large number of sympathomimetic amines which have been described in the published literature, relatively few compounds have in the last analysis shown sufficient effectiveness to have achieved substantial value in the relief of reversible obstructive lung conditions. The compounds which have been used for the practical clinical treatment of these conditions are the following:

Epinephrine

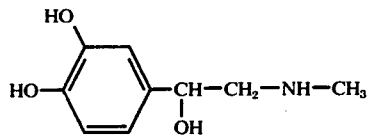

Epinephrine [1-(3',4'-dihydroxyphenyl)-2-(methylamino)-ethanol] given by injection has been and still is the drug of choice in the treatment of acute asthmatic attacks, but by inhalation it has now been almost completely replaced by isoprenaline [1-(3',4'-dihydroxyphenyl)-2-(isopropyl amino)-ethanol]. Epinephrine whether given by subcutaneous injection (0.2-0.5 ml of a 1 in 1,000 solution) or by aerosol inhalation of a 1% solution, is an effective drug in reversing airway obstruction. However, it stimulates $\alpha$- and $B_1$- as well as $\beta_2$-receptors and therefore causes tachycardia, increased cardiac output and sometimes an increase in blood pressure; and arterial oxygen desaturation may become worse.

Isoprenaline

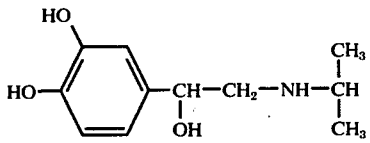

Isoprenaline is also an effective drug in relieving airway obstruction. However, it stimulates $\beta_1$ and $\beta_2$- receptors equally and it, too, has a tendency to produce therefore cardiovascular stimulation, especially tachycardia. Again, there may be no improvement in arterial oxygen desaturation, and in many instances, the PaO$_2$ falls. The cardiovascular effects are especially evident when the tablets (10 mg) are sucked or crushed in the mouth.

Most often, however, isoprenaline is given by inhalation either as a spray or from a portable pressurized aerosol. This latter device produces an aerosol mist the particles of which are of optimum size for a penetration deep into the lungs and for this reason it is all too easy for the patient to administer an overdose. Portable pressurized aerosols should be prescribed only when the doctor has satisfied himself that the patient fully understands the risks. Misuse of isoprenaline has been suggested as one of the most important causes of increased mortality in asthma primarily reported in England, where the use of isoprenaline aerosols achieved wide currency. Fortunately, since warnings about the dangers of overdosage from these aerosols have appeared, there has been a fall in asthma deaths.

The bronchodilator activity of epinephrine and isoprenaline is relatively short-lived, owing to rapid enzymic inactivation. When given with atropine methonitrate, the effect is prolonged, but it seems likely that because of the side effects and short duration of action these bronchodilators will in the future be superseded by new sympathomimetic amines such as the compounds of the present invention.

Ephedrine

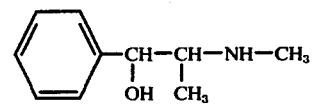

Ephedrine [1-phenyl-2-(methyl amino)propanol] has been used in this country for the oral treatment of chronic asthma alone or in combination with other drugs. Ephedrine, however, has considerable disadvantages, primarily a CNS-simulating effect which leads to anxiety and sleeping disturbances. Peripheral side effects are sweating, vasoconstriction and a contraction of the urogenital sphincters. Like other compounds, it also affects the heart, causing palpitations and tachycardia.

Orciprenaline

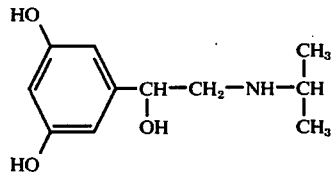

Orciprenaline has achieved substantial use in Europe as a bronchodilator. Orciprenaline is believed by some to be an improvement over both epinephrine and isoprenaline from the standpoint of longevity of action and reduced incidence of cardiovascular side effects. This compound, however, shows less potency than previously used bronchodilators. Orciprenaline has not been approved for use in this country.

In contrast to the foregoing, the compounds of the present invention have been found to exhibit improved selectivity for the bronchial muscles relative to the cardiovascular system. Because stimulation of the cardiovascular system is thought to be a cause of the adverse effects of many of the prior art compounds on blood oxygen pressures, it is expected that the compounds of the present invention will be less likely to lead to a fall in blood oxygen pressure then compounds such as epinephrine or isoprenaline. The compounds of formula II and physiologically acceptable acid addition salts thereof by known methods such as:

A. reduction of a diketo compound of the formula III in the presence of an amine of the formula IV according to the following reaction scheme:

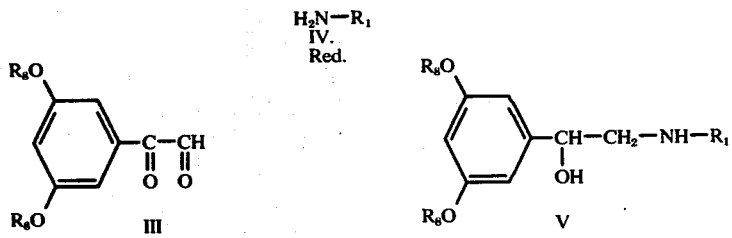

the present invention have the added advantage of improved longevity of action over all of the compounds described above. Moreover, it has been found that the specifically claimed compound terbutaline exhibits another important advantage in that it affords improved arteriel oxygen tension in asthmatic patients. This improvement has been observed in a number of clinical trials. It is believed that the improvement in arterial oxygen tension is related to a relaxation, by terbutaline, of small airways (i.e., airways less than 2 mm. in diameter) as well as large airways. This is a unique effect of terbutaline which clearly distinguishes terbutaline over previously used broncho-dilators.

These advantages are obtained according to the present invention by preparing compounds of the above whereafter $R_8$, if necessary, is replaced by hydrogen;

B. reaction of compounds of the formulas VI and VII according to the following reaction scheme:

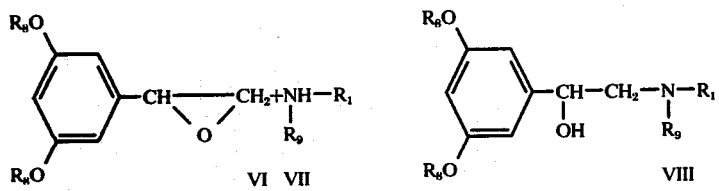

whereafter $R_8$ and $R_9$, if necessary, are replaced by hydrogen;

C. reduction of a compound of the formula IX according to the following scheme:

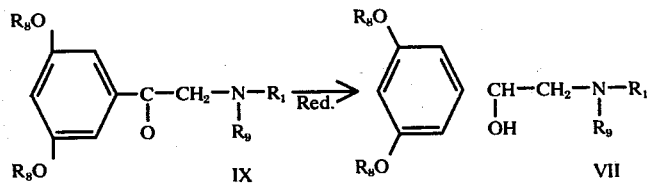

whereafter $R_8$ and $R_9$, if necessary, are replaced by hydrogen. In the formulas III to IX, $R_1$ is as defined above, $R_8$ is hydrogen or a group readily replaceable by hydrogen, such as for example alkyl or acyl radical of not more than 5 carbon atoms or mono or bicyclic aralkyl group of not more than 11 carbon atoms such as benzyl or naphthylmethyl and $R_9$ is hydrogen or a mono or bicyclic aralkyl group of not more than 11 carbon atoms.

D.

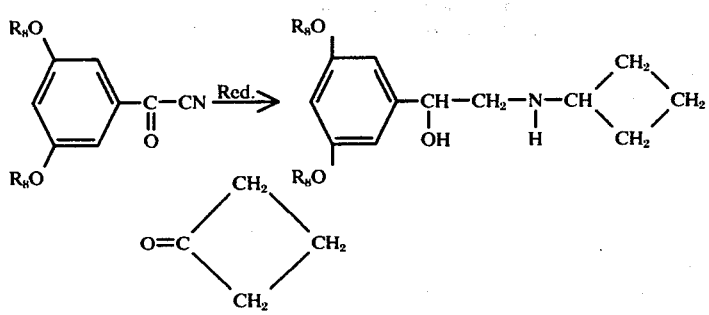

where $R_8$ has the above-stated meaning.

It will be appreciated that the compounds according to the invention exist in the form of optically active isomers. The isomers may be isolated, if desired, in a conventional manner.

The preferred method for the preparation of compounds of the formula II is Method C above. Starting materials of the formula IX can be obtained by a variety of routes. Some of the possible ways are outlined in the following reaction schemes where the numbers and letters underneath the arrows indicate an example illustrating the reaction: ml Scheme E

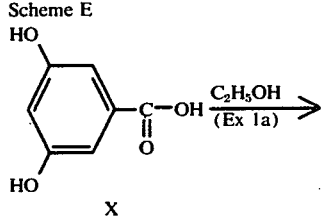
X

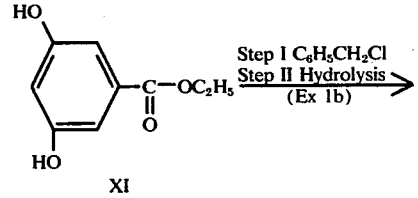
XI

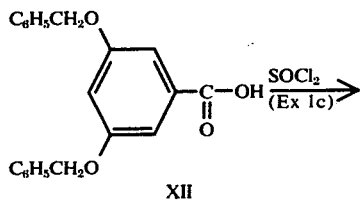
XII

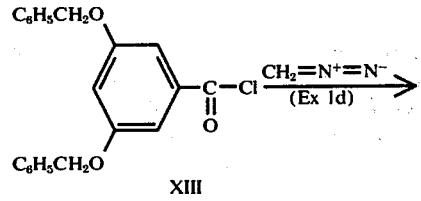
XIII

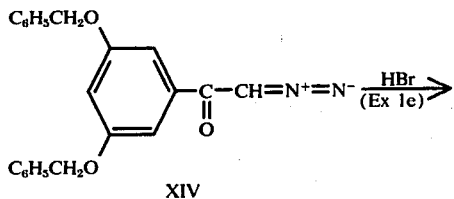
XIV

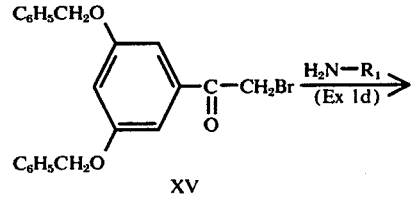
XV

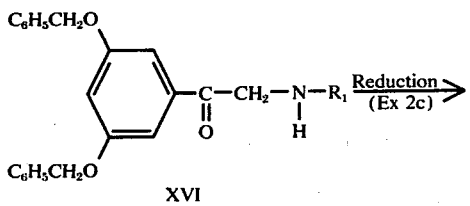
XVI

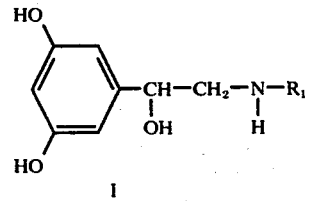
I

Scheme F.

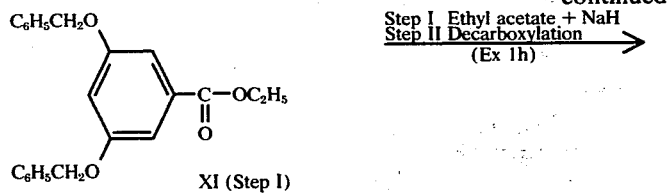
XI (Step I)

Step I Ethyl acetate + NaH
Step II Decarboxylation
(Ex 1h)

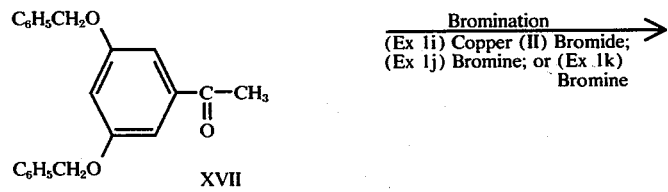
XVII

Bromination
(Ex 1i) Copper (II) Bromide;
(Ex 1j) Bromine; or (Ex 1k) Bromine

This compound is further treated as indicated under E above.

Scheme G.

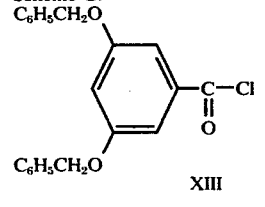
XIII

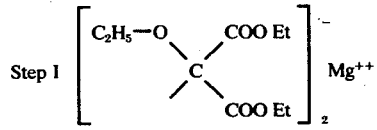
Step I

Step II Decarboxylation
(Ex 1g)

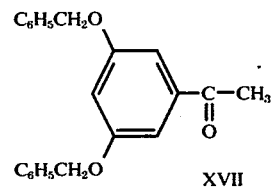
XVII

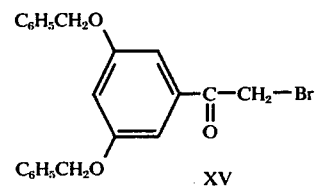
XV

This compound is further treated as indicated under Scheme E or F above.

Scheme H.

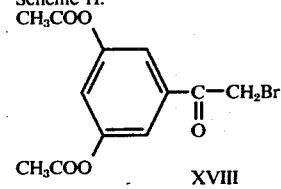
XVIII

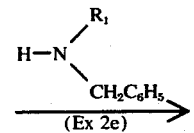
(Ex 2e)

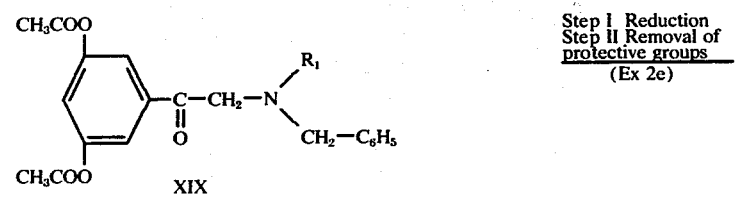
XIX

Step I Reduction
Step II Removal of protective groups
(Ex 2e)

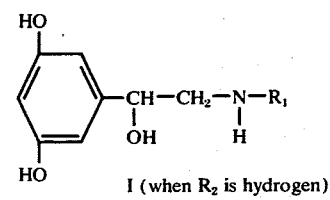
I (when $R_2$ is hydrogen)

Scheme I.

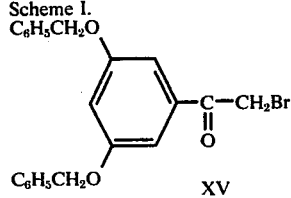
XV

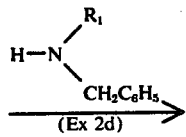
(Ex 2d)

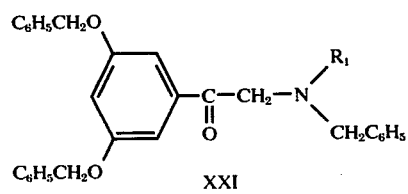
XXI (Ex 3) →

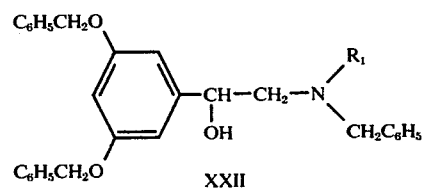
XXII

Replace benzyl groups →

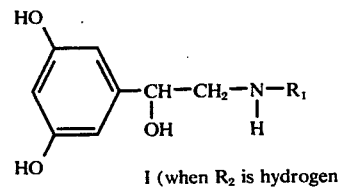
I (when $R_2$ is hydrogen)

Alternatively, Compound XXI may be directly hydrogenated to Compound I (when $R_2$ is hydrogen) as shown in Ex. 2 (d)

Scheme J. This scheme is a further illustration of Method A.

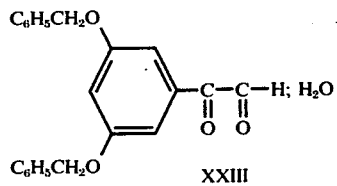
XXIII

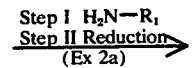
Step I $H_2N-R_1$
Step II Reduction
(Ex 2a)

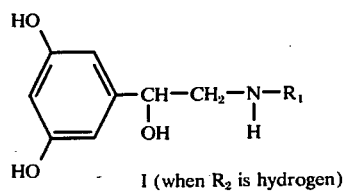
I (when $R_2$ is hydrogen)

Scheme K. This reaction scheme is a further illustration of Method D.

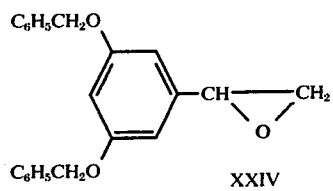
XXIV

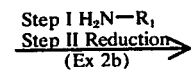
Step I $H_2N-R_1$
Step II Reduction
(Ex 2b)

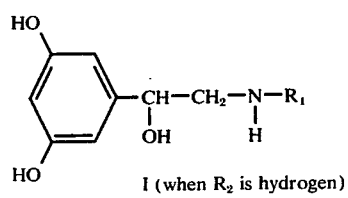
I (when $R_2$ is hydrogen)

Scheme L. This is a further illustration of Method D:

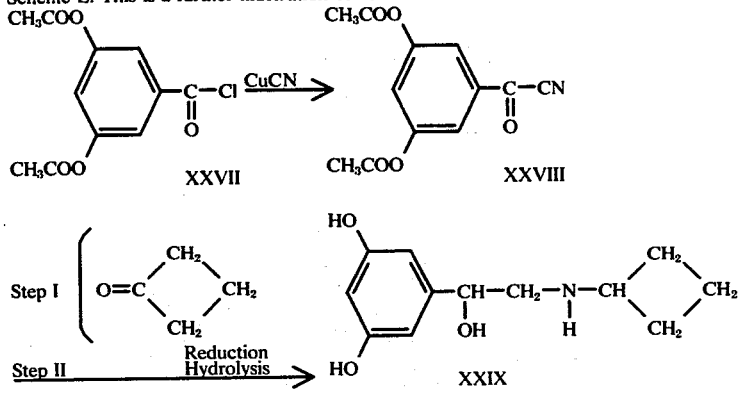

The reduction of the compound of the formula IX can be carried out for example a. by catalytic reduction, e.g. with Raney nickel or with palladium charcoal, or platinum oxide or b. chemical reduction, e.g. with lithium aluminum hydride or sodium borohydride in which case $R_8$ is a hydroxy-protective group, or c. chemical reduction of the carbonyl group, e.g. with lithium aluminum hydride or sodium borohydride, whereafter the hydroxy-protective groups $R_8$ and $R_9$ may be removed by catalytic reduction, e.g. with palladium charcoal or platinum oxide.

If in the formula VIII $R_8$ is an alkyl group, this can be replaced by hydrogen by ether-splitting agents, for example by using boron tribromide, at low temperature or by heating with hydrogen halides; in this case the alcoholic hydroxyl group is advantageously protected by acetylation, and the splitting carried out using hydrobromic acid in anhydrous glacial acetic acid or glacial acetic acid/acetic anhydride, and then hydrolyzed. If in the formula VIII $R_8$ is an acyl residue, this can be split off by treatment with acids if the free hydroxy compound is desired. If in the formula VIII $R_8$ and $R_9$ means aralkyl, this can be removed by hydrogenolysis.

The new 1-(3',5'-dihydroxyphenyl)-2-alkylaminoethanols and 1-(3',5'-diacyloxyphenyl)-2-alkylaminoethanols of the instant invention are very good bronchodilators and have only very weak cardioaccelerating effect in therapeutically effective doses. Thus in both in vitro and in vivo the compound 1-(3',5'-dihydroxyphenyl)-2- (t-butylamino)-ethanol (which has been given the generic name "terbutaline") has proved to be a more potent bronchodilator than 1-(3',5'-dihydroxyphenyl)-2-(isopropylamino)-ethanol (orciprenaline) and the duration of the effect of terbutaline is longer than that of orciprenaline. Parallel tests showed that the cardioaccelerating effect of terbutaline is significantly less than that of orciprenaline. This relation between the heart stimulatory effect and the bronchodilator effect has been demonstrated, for example, in spontaneously beating guinea pig auricle preparation and spirally cut trachea preparation, both preparations being immersed in the same bath. [This procedure is more fully described below in Example 5(b)]. When the compound according to the present invention was slowly infused in the bathing solution a bronchodilation was obtained without any effect on the heart muscle preparation. The weak cardioaccelerating effect of the t-butylamino compound according to the invention has also been verified in circulatory studies of the compound in anesthetized cat.

The weakening of the cardioaccelerating effect is thus obtained by replacing a secondary open chain carbon atom with a tertiary one or making it part of a cycloalkyl group. Although the compound of formula I specifically described herein is one in which the group $R_1$ is t-butyl, such compounds in which the group $R_1$ is cyclobutyl are also included within the scope of the invention. The essential feature is that the tertiary carbon atom or the cycloalkyl group is linked directly to the nitrogen atom.

The new compounds according to the invention may be administered in the form of salts with physiologically acceptable acids. Suitable acids which may be used are, for example, hydrochloric, hydrobromic, sulphuric, fumaric, citric, tartaric, maleic or succinic acid.

The invention further provides pharmaceutical compositions comprising as active ingredient at least one of the compounds according to the invention in association with a pharmaceutical carrier. Such compositions may be desgned for oral, bronchial, rectal or parenteral administration.

To produce pharmaceutical preparations in the form of dosage units for oral application containing a compound of the invention in the form of the free base, or a pharmaceutically acceptable salt thereof, the active ingredient may be mixed with a solid, pulverized carrier, for example, lactose, saccharose, sorbitol, mannitol, a starch such as potato starch, corn starch, maize starch or amylopectin, a cellulose derivative or gelatin, and also may include lubricants such as magnesium or calcium stearate or a Carbowax or other polyethylene glycol waxes and compressed to form tablets or centers for dragees. If dragees are required, the centers may be coated, for example, with concentrated sugar solutions which may contain gum arabic, talc and/or titanium dioxide, or alternatively with a lacquer dissolved in easily volatile organic solvents or mixtures of organic solvents. Dyestuffs can be added to these coatings. For the preparation of soft gelatin capsules (pearl-shaped closed capsules) consisting of gelatin and, for example, glycerol, or similar closed capsules, the active substance may be admixed with a Carbowax. Hard gelatin capsules may contain granulates of the active substance with solid, pulverized carriers such as lactose, saccharose, sorbitol, mannitol, starches (for example potato starch, corn starch, or amylopectin), cellulose derivatives or gelatin, and may also include magnesium stearate or stearic acid. Dosage units for rectal application may be in the form of suppositories comprising the active substance in admixture with a neutral fatty base, or gelatin rectal capsules comprising the active substance in admixture with a Carbowax or other polyethylene glycol waxes. Each dosage unit preferably contains 0.5 to 50 mg of active ingredient.

Liquid preparations for oral application may be in the form of syrups, suspensions or emulsions, for example containing from about 0.1% to 20% by weight of active substance and also, if desired, such adjuvants as stabilizing agents, suspending agents, dispersing agents, flavoring agents and/or sweetening agents.

Liquid preparations for rectal administration may be in the form of aqueous solutions containing from about 0.1% to 2% by weight of active substance and also, if desired, stabilizing agents and/or buffer substances.

For parenteral application by injection the carrier may be a sterile, parenterally acceptable liquid, e.g., pyrogen-free water or an aqueous solution of polyvinylpyrrolidone, or a parenterally acceptable oil, e.g., arachis oil and optionally stabilizing agents and/or buffer substances. Dosage units of the solution may advantageously be enclosed in ampoules, each dosage unit preferably containing from 0.05 to 5 mg of active ingredient.

For administration to the bronchia, the compositions are advantageously in the form of a spray solution or spray suspension. The solution or suspension advantageously contains from 0.1 to 10% by weight of the active ingredient.

The present invention is fully illustrated by the following examples of the synthesis and use of the compounds which have been discovered:

A. Examples 1–4 illustrate the basic principles of the synthesis of the dihydroxyphenyl compounds.

B. Example 5 and FIGS. 1-8 show the ability of terbutaline to selectively bring about relaxation of the bronchial muscles.

C. Example 6 and FIG. 9 illustrate the practical application of terbutaline to the treatment of asthma.

D. Examples 7 and 8 show pharmacological effects of the corresponding cyclobutyl compounds [1-(3',5'-dihydroxyphenyl)-2-cyclobutylamino ethanol] as measured in laboratory tests.

E. Example 9 sets forth toxicity data on the compounds of this invention.

F. Example 10 illustrates the resolution of the compounds of the present invention into their optical isomers.

G. Examples 11 and 12 set forth synthesis procedures for the preparation of the 3',5'-diacyloxyphenyl compound of the present invention.

H. Examples 13 to 18 set forth the results of pharmacological tests of 3',5'-diacyloxyphenyl analogues of terbutaline; and I. Examples 19 to 27 illustrate various pharmaceutical preparations into which the present invention may be formulated. In the following Examples the Figures referred to are:

A. Synthesis of Dihydroxyphenyl Compounds

Figure 1:
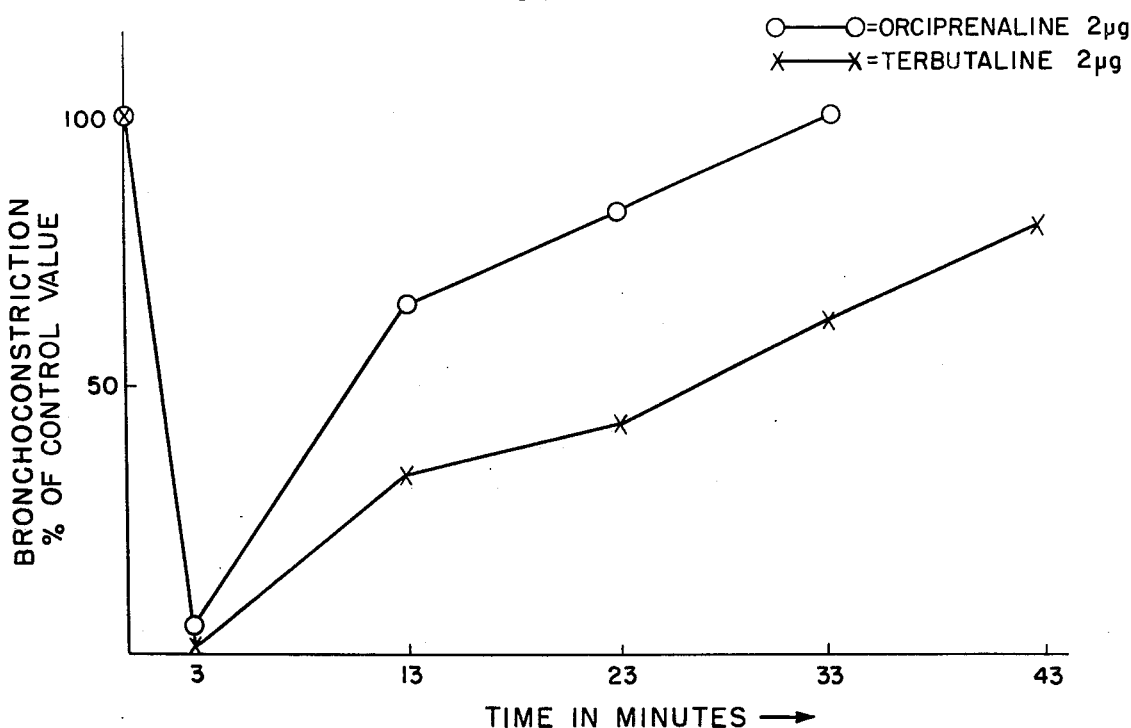
FIG. 1 illustrates the duration of the effect of terbutaline and orciprenaline against histamine induced bronchoconstriction (guinea pig 0.95 kg), bronchospasmolytic effect being determined according to the method of Konzett & Rossler.

Example 1.

Preparation of 3,5-dibenzyloxy-ω-(t-butylamino)-acetophenone used as a starting material.

a. Ethyl 3,5-dihydroxybenzoate 308 g. of α-resorcylic acid were dissolved in 1000 ml of absolute ethanol and 25 ml of concentrated sulphuric acid were added. The reaction mixture was boiled under reflux for 20 hours. The ethanol was evaporated and the residue poured into water and extracted with ether. The etheral phase was washed with sodium bicarbonate solution and water and dried with magnesium sulphate. When the ether was evaporated, a crystallizing residue was obtained.

b. 3,5-Dibenzyloxybenzoic acid

In a two-liter three necked flask supplied with a stirrer and a reflux condenser 221 g of ethyl 3,5-dihydroxybenzoate, 750 ml of absolute ethanol, 360 ml of benzyl chloride and 210 g of potassium carbonate were introduced. The reaction mixture was boiled under reflux, stirred for 20 hours and filtered hot. The ethanol was evaporated and to the residue water and sodium hydroxide were added to alkaline reaction. The water phase was extracted with ether and the ether phase dried with magnesium sulphate. The ether was evaporated and remaining benzyl chloride was distilled off under reduced pressure. The remaining oil was refluxed for three hours on a water bath with 150 g of potassium hydroxide in 750 ml of ethanol and 50 ml of water. The ethanol was evaporated and 250 ml of water were added. On acidifying the solution with 5 N hydrochloric acid, the 3,5-dibenzyloxybenzoic acid crystallized. It was crystallized from ethyl acetate: M.p. 214–216° C.

c. 3,5-Dibenzyloxy-benzoyl-chloride 167 g of 3,5-dibenzyloxybenzoic acid and 400 ml of redistilled thionyl chloride were refluxed on an oil bath for one hour. Excess thionyl chloride was distilled off at reduced pressure, and the remaining mass crystallized. The product was recrystallized from petroleum ether (B.p., 60°–85° C.) : M.P. 73°–74° C.

d. 3,5-Dibenzyloxy-diazo-acetophenone

Diazomethane was prepared by slowly adding 86 g of N-nitroso-o-toluenesulphomethylamide in ether to a solution of 24 g of potassium hydroxide in 40 ml of water and 100 ml of diethylene-glycol monoethyl ether in 40 ml of ether. The reaction flask was heated to 55°–65° C. on a water bath, and the diazomethane formed was distilled with ether into a receiver containing 71 g of 3.5-dibenzyloxybenzoyl-chloride in 250 ml of absolute ether at -25° C. The reaction mixture was slowly allowed to reach room temperature. The ether solution was directly used in the next reaction.

e. 3,5-Dibenzyloxy-ω-bromoacetophenone

To the ether solution from the previous reaction were added 300 ml of benzene and ether saturated with hydrogen bromide until the evolution of nitrogen ceased. When the solution was evaporated, the residue crystallized. The crystals were dissolved in xylene, precipitated with petroleum ether (B.p. 40°–60° C.) and washed with absolute ether: M.p. 82°–84° C. In a similar manner 3,5-dibenzyloxy-ω-chloroacetophenone was prepared. M.p. 78°–80° C.

f. 3,5-Dibenzyloxy-ω-(t-butylamino)-acetophenone 1.5 g of t-butylamine and 85 ml of absolute ethanol were placed in a 250 ml flask provided with a reflux condenser and the mixture was heated to reflux. The reaction was performed under nitrogen. At the reflux temperature, 4.1 g of 3,5-dibenzyloxy-ω-bromoacetophenone in 15 ml of benzene were added. The mixture was refluxed for 20 hours and after evaporation a yellow oil was recovered. This oil was shaken with absolute ether and white crystals were formed (t-butylamine hydrobromide). The crystals were filtered off and washed with ether. To the combined ether phases 10% hydrobromic acid was added and a white precipitate was formed. This precipitate was filtered off, thoroughly washed with water and ether, and recrystallized from ethanol: M.p. 196°–198° C.

g. 3,5-Dibenzyloxyacetophenone 70 g of 3,5-dibenzyloxy-benzoyl-chloride in dry benzene were slowly added to a solution of diethyl ethoxymagnesium-malonate prepared in known manner. The reaction mixture was refluxed overnight, and after cooling 300 ml of benzene and 200 ml of 5-N sulphuric acid were added to hydrolyze the mixture. The benzene phase was washed three times with water and dried with magnesium sulphate. The benzene was evaporated and the excess of diethyl malonate distilled off under reduced pressure. To the residue 400 ml of dioxane, 80 ml of water and 40 ml of conc. hydrochloric acid were added. The reaction mixture was heated for 24 hours on an oil bath at 130° C. After evaporation a brown oil remained, which crystallized on standing. Recrystallized from ethanol: M.p. 60°–61° C.

h. 3,5-Dibenzyloxyacetophenone 5.0 g of 50% sodium hydride suspension and a few ml of benzene were introduced in a 500 ml three-necked flask, supplied with a stirrer, reflux condenser and dropping funnel. 18.1 g of ethyl 3,5-dibenzyloxybenzoate in 150 ml of dry benzene were added. The reaction mixture was stirred and heated on an oil bath (90°–100° C.), and 4.5 g of ethyl acetate in 25 ml of dry benzene were slowly added and then heated and stirred for 7 hours. The reaction mixture was cooled. A few ml of ethanol were added and the whole was then poured into 150 ml of 50% acetic acid solution. The acidic water phase was extracted with ether. The ether phase was washed with water, sodium bicarbonate solution and water, and then dried with magnesium sulphate. After evaporation an oil was recovered. This oil was treated with 80 ml of dioxane, 16 ml of water and 8 ml of concentrated hydrochloric acid and the mixture was heated on an oil bath at 130°–140° C. for 15 hours. After evaporation, ether was added and the ether phase washed with water, 2-N sodium hydroxide solution and water. The ether phase was then evaporated and the residue was dissolved in hot ethanol and 200 ml of 1-N sodium hydroxide solution was added. The mixture was refluxed for five hours in order to hydrolyze remaining ethyl 3,5-dibenzyloxybenzoate. The ethanol was evaporated and the water phase extracted with ether. The ether phase was washed with water, dried with magnesium sulphate and evaporated. The remaining oil crystallized from petroleum ether (B.p. 80°–110° C.). M.p. 61.5°–62.0° C.

i. 3,5-Dibenzyloxy-ω-bromoacetophenone 11.2 g of copper (II) bromide were placed in a three-necked flask provided with a stirrer and a reflux condenser. 25 ml of ethyl acetate were added and the mixture was heated to reflux under stirring. 10 g of 3,5-dibenzyloxyacetophenone in 30 ml of hot chloroform were added and the reflux was continued until the black-green color changed to light brown. The copper (I) bromide formed was filtered off, and after evaporation of the filtrate a brown oil was recovered which soon crystallized. Recrystallized from ethanol: M.p. 82°–84° C. Alternatively this step i) may be replaced by j) or k).

j. 3,5-Dibenzyloxy-ω-bromoacetophenone

In a 250 ml three-necked flask, supplied with a stirrer and a reflux condenser and a dropping funnel, 5.0 g of 3.5-dibenzyloxyacetophenone in 90 ml chloroform were introduced. Then 15 drops of glacial acetic acid saturated at 0° C. with hydrogen bromide were added to the solution. 4 ml of a solution prepared from 2.4 g of bromine and 25 ml chloroform were added. The reaction mixture was heated to reflux and then rapidly cooled to 0° C. The remaining bromine solution was slowly added under stirring and cooling, and then stirred for another hour at room temperature and finally heated for half an hour at reflux temperature. After cooling to room temperature nitrogen was introduced to remove remaining hydrogen bromide. Petroleum ether (B.p. 60°–85° C.) was added and the reaction mixture was washed with cold sodium bicarbonate solution and water saturated with sodium chloride. The organic phase was dried with magnesium sulphate and evaporated. The remaining oil crystallized on standing. Recrystallized from ethanol: M.p. 85°–84° C.

k. 3,5-Dibenzyloxy-ω-bromoacetophenone 20.0 g of 3,5-dibenzyloxyacetophenone were dissolved in 460 ml of dry ether and cooled to 0° C. 9.7 g of bromine dissolved in 30 ml of dry, ethanol-free chloroform were added slowly. During the addition, the temperature was kept at 0° C. The temperature of the reaction mixture was then allowed to rise to room temperature and was kept there for 2.5 hours under stirring. The ether was then evaporated at room temperature and an oil was recovered, which soon crystallized. The product is identical with that received in Example 1j).

EXAMPLE 2.

Preparation of 1-(3′,5′-dihydroxyphenyl)-2-(t-butylamino)-ethanol and its salts a. To a solution of 6.8 g of the hydrate of 1-glyoxyl-oyl-3,5-dibenzyloxy-benzene in 50 ml of methanol were added 7.0 g of t-butyl-amine and 30 ml of benzene. The reaction mixture was refluxed for three hours and evaporated. The remaining oil crystallized when ethanol was added. M.p. 78.5°–79.5° C. 2.5 g of this compound in 75 ml absolute ethanol were hydrogenated under normal conditions with Raney nickel. After filtering off the catalyst and evaporation, the remaining oil was dried with ethanol/benzene. The base in ethanol was treated with hydrogen bromide in ethanol and evaporated. The residue can be crystallized from glacial acetic acid/chloroform.

The IR spectrum of this product is identical with that of the product in 2c).

b. To a solution of 3.5g of 3′,5′-dibenzyloxyphenyl-epoxyethane in 100 ml of ethanol was added 2.7 g of t-butylamine in 20 ml of ethanol. The reaction mixture was refluxed for 4 hours and then evaporated. The crystalline residue can be recrystallized from absolute ether. The melting point of 1-(3′,5′-dibenzyloxyphenyl)-2-(t-butylamino)-ethanol is 119°–122° C. The preparation of salt and the reduction can be performed in the same way as described under 2a).

c. 2.4 g of 3.5-dibenzyloxy-ω-(t-butylamino)-acetophenone hydrobromide in 200 ml of glacial acetic acid were hydrogenated in the presence of 0.3 g of 10% palladium charcoal at room temperature and normal pressure. Ethanol was added to dissolve precipitated reaction product. The catalyst was filtered off and the residue evaporated to dryness, 50 ml absolute ethanol was added and the solution hydrogenated in the presence of 0.3 g of 10% palladium charcoal at 35° C. and 5 atmospheres pressure. The catalyst was filtered off and the residue evaporated to dryness. It was recrystallized from glacial acetic acid and chloroform: M.p. 93°–97° C., for the monohydrate. The non-hydrated compound has the melting point 205°–206° C. (decomposition).

d. To a solution of 32 g of benzyl-t-butylamine in 300 ml of absolute ethanol at reflux temperature was added 32 g of 3,5-dibenzyloxy-ω-bromoacetophenone in 10 ml of dry benzene. The mixture was refluxed for twenty hours and then evaporated. When absolute ether was added to the residue, benzyl-t-butylamine hydrobromide was precipitated. The precipitated compound was filtered off and to filtrate was added an excess of 2 N sulphuric acid. This caused precipitation of the hydrogen sulphate of 3,5-dibenzyloxy-ω-(benzyl-t-butylamino)-acetophenone which was recrystallized from acetone/ether If the product is crystallized from different organic solvents, the melting point will vary with the type and amount of solvent of crystallization, but the product can be used directly for hydrogenation.

15 g of 3.5-dibenzyloxy-ω-(benzyl-t-butylamino)-acetophenone hydrogen sulphate in 200 ml of glacial acetic acid were hydrogenated in a Parr pressure reaction apparatus in the presence of 1.5 g of 10o% palladium charcoal at 50° C. and five atmospheres pressure. The reaction time was 5 hours. The catalyst was filtered off, the filtrate was evaporated to dryness and the hydrogen sulphate of 1-(3′,5′-dihydroxyphenyl)-2-(t-butylamino)-ethanol was received. This compound is hygroscopic, but it can be transformed into a non-hygroscopic sulphate in the following manner.

The hydrogen sulphate was dissolved in water and the pH of the solution was adjusted to 5.6 (pH-meter) with 0.1 N sodium hydroxide solution. The water solution was evaporated to dryness and the residue dried with absolute ethanol/benzene and once more evaporated to dryness. The remaining crystal mixture was extracted in a Soxhlet extraction apparatus with absolute methanol. From the methanol phase the sulphate of 1-(3′,5′-dihydroxyphenyl)-2-(t-butylamino)-ethanol crystallized. M.p. 246°–248° C.

The sulphate can also be prepared in the following manner: After the hydrogenation with palladium charcoal in glacial acetic acid the catalyst was filtered off. At elevated temperature the theoretical amount of anhydrous sodium acetate was added, the solution stirred for five minutes, at which time the sodium sulphate was precipitated and then filtered off from the hot solution. From the filtrate the sulphate of 1-(3′,5′-dihydroxyphenyl)-2-(t-butylamino)-ethanol was isolated.

e. To 6.3 g of 3,5-diacetoxy-ω-bromoacetophenone dissolved in 100 ml of dry benzene were added 7.0 g of benzyl-t-butylamine in 50 ml of dry benzene. The mixture was refluxed for three hours and then evaporated. When absolute ether was added to the residue, benzyl-t-butylamine hydrobromide was precipitated and filtered off. The ether phase was treated with hydrogen bromide in ether until the solution was slightly acid.

The precipitated salt mixture was treated with water in order to dissolve benzl-t-butylamine hydrobromide. The crystals were filtered off, washed with water and recrystallized by dissolving in ethanol and precipitating with absolute ether. The hydrobromide of (3,5-diacetoxy)-ω-(benzyl-t-butylamino)-acetophenone has the M.p. 171°–173° C.

1.1 g of this salt were dissolved in warm absolute ethanol and 0.1 g 10% palladium charcoal were added. The solution was then hydrogenated at 50° C. and 5 atmospheres pressure overnight. The catalyst was filtered off and the volume of the solution reduced by evaporation. The hydrobromide of 1-(3′,5′-diacetoyphenyl)-2-(t-butylamino)-ethanol with one mole of water was precipitated by the addition of ether. M.p. 108°–111° C. The protective acetyl groups may be removed by boiling the 1-(3′,5′-diacetoxyphenyl)-2-(t-butylamino)-ethanol hydrobromide with 1% hydrobromic acid for 3 hours. After evaporation and drying the product was recrystallized as described in Example 2c).

EXAMPLE 3.

Preparation of 1-(3′,5′-dibenzyloxyphenyl)-2-(benzyl-t-butylamino)-ethanol

To 18.3 g of 3′,5′-dibenzyloxy-ω-(benzyl-t-butylamiro)-acetophenone in ethanol were added 2 g of sodium borohydride. The reaction mixture was allowed to stand overnight. Some methanol was added and the solution was evaporated. To the residue was added water and 2-N sodium hydroxide solution and the water phase was extracted with ether. The ether phase was dried with magnesium sulphate. The ether was evaporated and an oil was collected, which crystallized on standing. M.p. 78°–79° C. The resulting 1-(3′,-

5'-dibenzyloxyphenyl)-2-(benzyl-t-butylamino)-ethanol can be converted to the corresponding 1-(3',-5'-dihydroxyphenyl)-2-(t-butylamino)-ethano by replacing benzyl groups with hydrogen in a known manner.

EXAMPLE 4.

Preparation of 1-(3',5'-dihydroxyphenyl)-2-(cyclobutylamino)-ethanol hydrobromide 5.5 g of benzyl-cyclobutylamine were dissolved in 100 ml of absolute ethanol and 7.0 g of 3,5-dibenzyloxy-ω-bromoacetophenone in 30 ml of dry benzene were added to this solution. The reaction mixture was refluxed overnight and then evaporated. When absolute ether was added to the residue, the benzyl-cyclobutylamine hydrobromide was precipitated and filtered off. With the addition of 10% hydrobromic acid to the filtrate, the 3,5-dibenzyloxy-ω-(benzyl-cyclobutylamino)-acetophenone hydrobromide was precipitated. It was recrystallized from acetone/ether. M.p. 85°–88° C.

4.2 g of the recrystallized product were dissolved in ethanol and 0.5 g of 10% palladium charcoal were added. The hydrogenation was performed in a Parr pressure reaction apparatus at 50° C. and five atmospheres pressure. The reaction time was about 15 hours. The catalyst was filtered off and on evaporation the product crystallized. It was recrystallized from ethanol/ether. The melting point of 1-(3',5'-dihydroxyphenyl)-2-(cyclobutylamino)-ethanol hydrobromide is 227°–228° C.

B. Pharmacological Tests of Terbutaline

The present invention may be more fully understood by the following example of the pharmacological properties of the novel compounds claimed herein.

EXAMPLE 5 a. Bronchospasmolytic effect in vitro.

The effect of the relaxation of isolated bronchial muscle of a racemic mixture of terbutaline was compared with epmephrine and orciprenaline on spirally cut trachea from the guinea pig according to the method originally described by Castillo and Beer [J. Pharacol. Exp. Ther. 90 (1947) page 104 ] and later modified by Constantine [J. Pharm. Pharmacol. 17 (1965) page 384].

In this test, guinea pigs are stunned with a blow on the head and bled to death. The trachea is dissected out, cut spirally and mounted in an organ bath (25 ml) in Krebs solution continuously aerated with oxygen (95%) and carbon dioxide (5%). Pilocarpine (1 μg/ml) is added to bring the preparation into a state of contraction. The tension of the preparation is measured and is usually about 2 gm. initially. Dose response curves for epinephrine and each of the test compounds are then evaluated on the same muscle preparation. All comparisons of potency are made at $ED_{50}$ values (i.e., micrograms/ml) of compound needed to produce 50% relaxation of the trachea. When tested in accordance with this procedure the compound of the present invention, terbutaline, was found to be about two times as active as orciprenaline and slightly less potent than -epinephrine.

b. Bronchospasmolytic effect in vivo

Orciprenaline and terbutaline were also tested in vivo according to the method described by Konzett and Rossler [Arch. Exp. Path. Pharmak. 195 (1940) page 71]. In the method of Konzett and Rossler, the animal is ventilated with a constant volume of air. When a certain pressure has been reached in the lung, the volume of air which is in excess of the pulmonary capacity will escape through the valve. This surplus of air is recorded. In testing compounds in the Konzett and Rossler method, bronchial contraction is provoked by administration of histamine. The histamine reduced the capacity of the airways, and the measured overflow increases. In order to see to what extent a test compound counteracts the histamine-induced bronchospasm, the animal is first given an injection of the test compound which is followed three minutes later by exposure to histamine. Comparison of the overflow measured in the protected animal with the overflow induced by a non-protected animal following exposure to histamine shows the effectiveness of various compounds to control the bronchospastic effect of histamine.

The bronochospasmolytic effect of terbutaline measured in accordance with the Konzett and Rossler procedure was compared with the effect of orciprenaline, both compounds being administered intravenously. The results are graphically shown in FIG. 1. As can be seen for most of the period of the test, terbutaline was in the order of twice as effective as orciprenaline in controlling histamine-induced bronochospasms.

Similar results were obtained when the cyclobutyl compound was tested. The bronochospasmolytic effect of 1-(3',5'-dihydroxyphenyl)-2-cyclobutylamino)-ethanol when measured as described above was found to be about 1.2 times as active as orciprenaline and about 0.4 times as active as epinephrine.

c. Effect on heart, dual preparation test, in vitro

The relation between the heart stimulatory effect and bronochodilator effect was studied in vitro on auricle-trachea-preparation from the guinea pig in order to compare the effect on the heart and the effect on the bronchial muscle under identical experimental conditions. Both spontaneously beating auricle and spirally-cut trachea were placed in the same bath in Krebs solution. Both preparations were taken from the same animal.

The compound to be tested was slowly infused into the bathing solution and the tension was measured for each of the auricle and tracheal preparations. As the concentration of the compound rose with time, it was easy to observe on which muscle the test compound was more effective and the time (or concentration) at which the effect became observable.

In carrying out this dual preparation test, epinephrine was used as a reference. Epinephrine causes bronchodilation and heart muscle stimulation in the same concentration range. Infusion of epinephrine was made over a period of ten minutes. After washing and recovery, the test solution was infused in the same manner and the effect of the test compound was compared with the effect of epinephrine.

Figure 2:
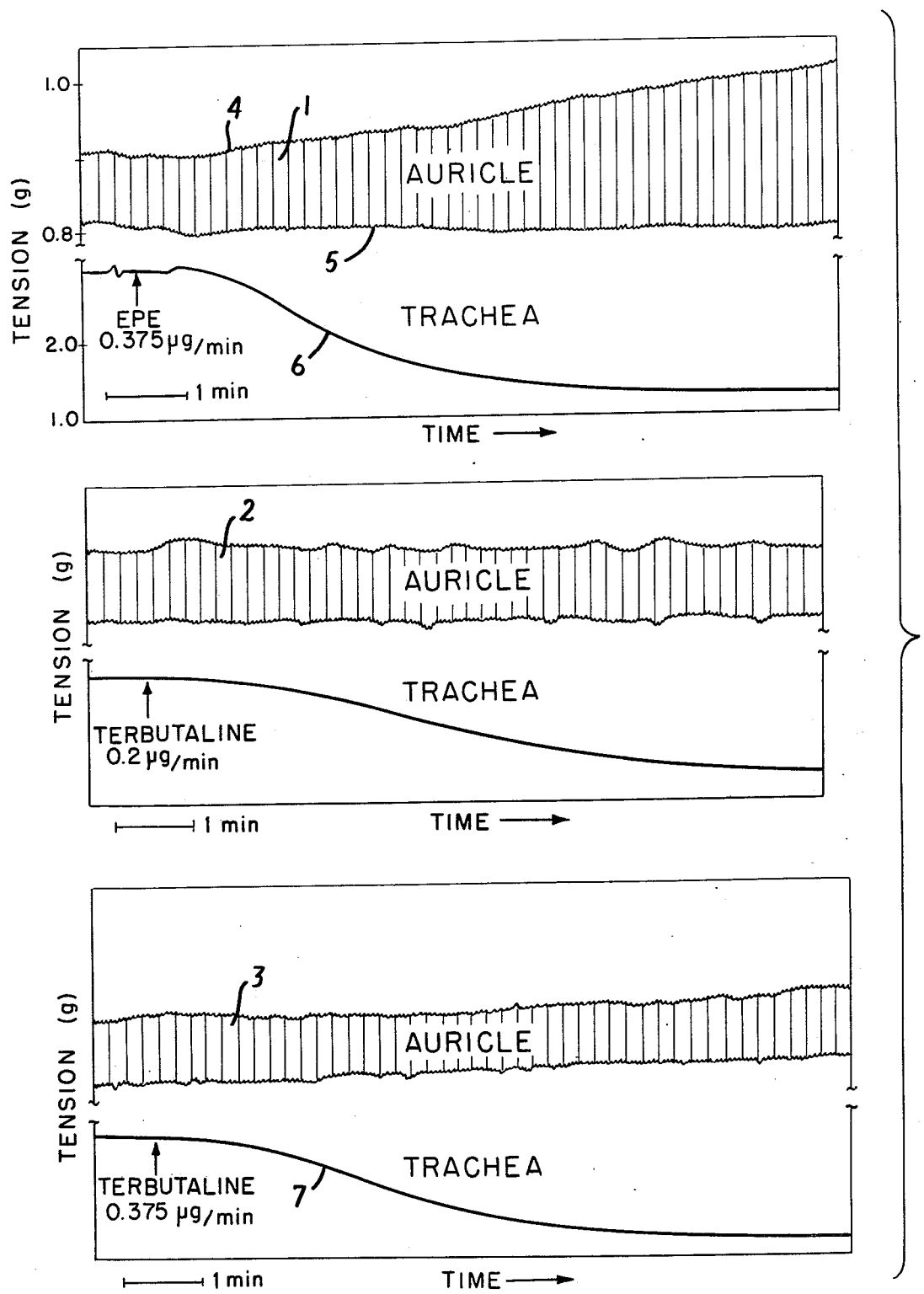
FIG. 2 illustrates the effect of epinephrine (EPE) and terbutaline on spirally cut trachea and right auricle from the guinea pig. Both preparations are dissected out from the same animal and run under identical experimental conditions.

FIG. 2 sets forth a typical result of this experiment comparing the effect of epinephrine with the effect of terbutaline infused at two different rates. In a like manner, epinephrine is compared, in FIG. 3, with norepinephrine (NE) and isoprenaline (IPR), and FIG. 4 compares epinephrine with orciprenaline.

Referring more specifically to FIG. 2, the upper portion of each chart thereof represents the tension continuously recorded of the auricle preparation (shaded area 1 for the effect of epinephrine on the auricle, ref. no. 2 for the effect of terbutaline infused at a rate of 0.2 μg/min on the auricle, and ref. no. 3 for the effect of terbutaline infused at a rate of 0.375μg/min on the auricle). The upper boundary of each of the shaded areas (for example, ref. no. 4 of the shaded area 1) represents the maximum tension of the spontaneously beating auricle while the lower boundary (ref. no. 5 of shaded area 1) represents the minimum tension of the spontaneously beating auricle.

As can be seen in FIG. 2, as epinephrine is infused, the maximum tension of the spontaneously beating auricle increases with time, and increasing concentration of epinephrine (ref. no. 1 of FIG. 2). By contrast, during the time period when epinephrine infused at a rate of 0.375 micrograms/minutes nearly doubled the maximum tension of the aurcile, terbutaline infused at the same rate (ref. no. 3 of FIG. 2) had little observable effect on the auricle.

The concurrent measurements of the relaxation of the tracheal preparation in the same test show that while terbutaline had little effect on the auricle, its effect on the trachea was nearly as potent as the effect of epinephrine. Thus, referring to FIG. 2, there is shown the relaxation of the tracheal muscle upon infusion of 0.375 μg/minute of epinephrine (ref. no. 6). It is apparent that epinephrine is affecting both the auricle and tracheal preparations over the concentration range tested. This same measurement of the relaxation of the tracheal muscle for terbutaline (ref. no. 7 of FIG. 2) shows that terbutaline infused at a rate of 0.375 μg/minute had an effect on the tracheal muscle nearly comparable to that of epinephrine infused at the same rate.

Figure 3:
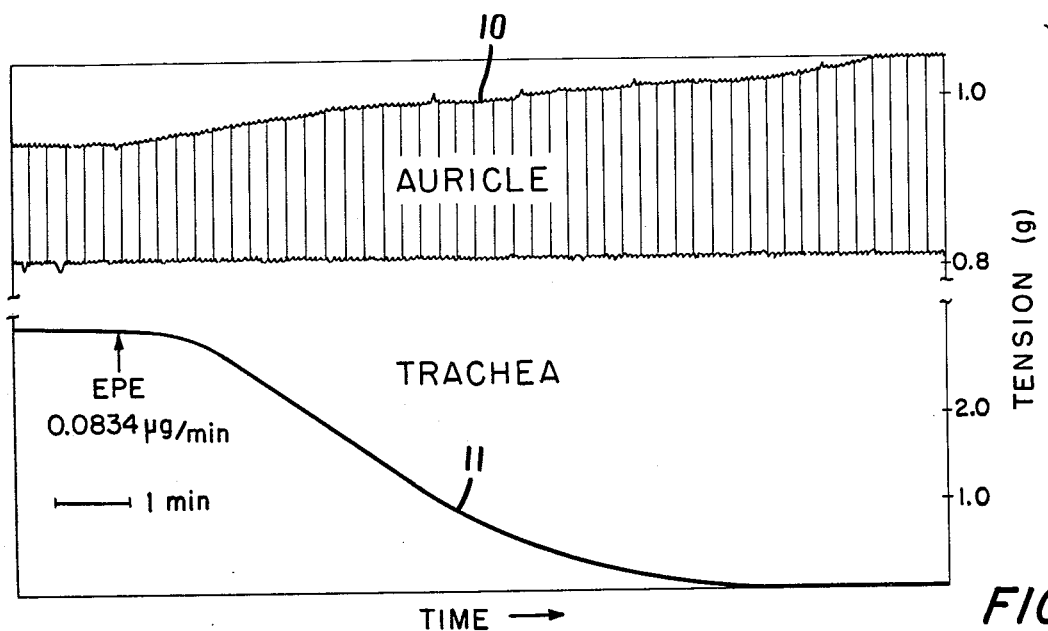
FIG. 3 shows the effect of epinephrine (EPE), norepinephrine (NE) and isoprenaline (IPR) on spirally cut trachea and right auricle from the guinea pig. Both preparations are dissected out from the same animal, and run under identical experimental conditions.
Figure 3:
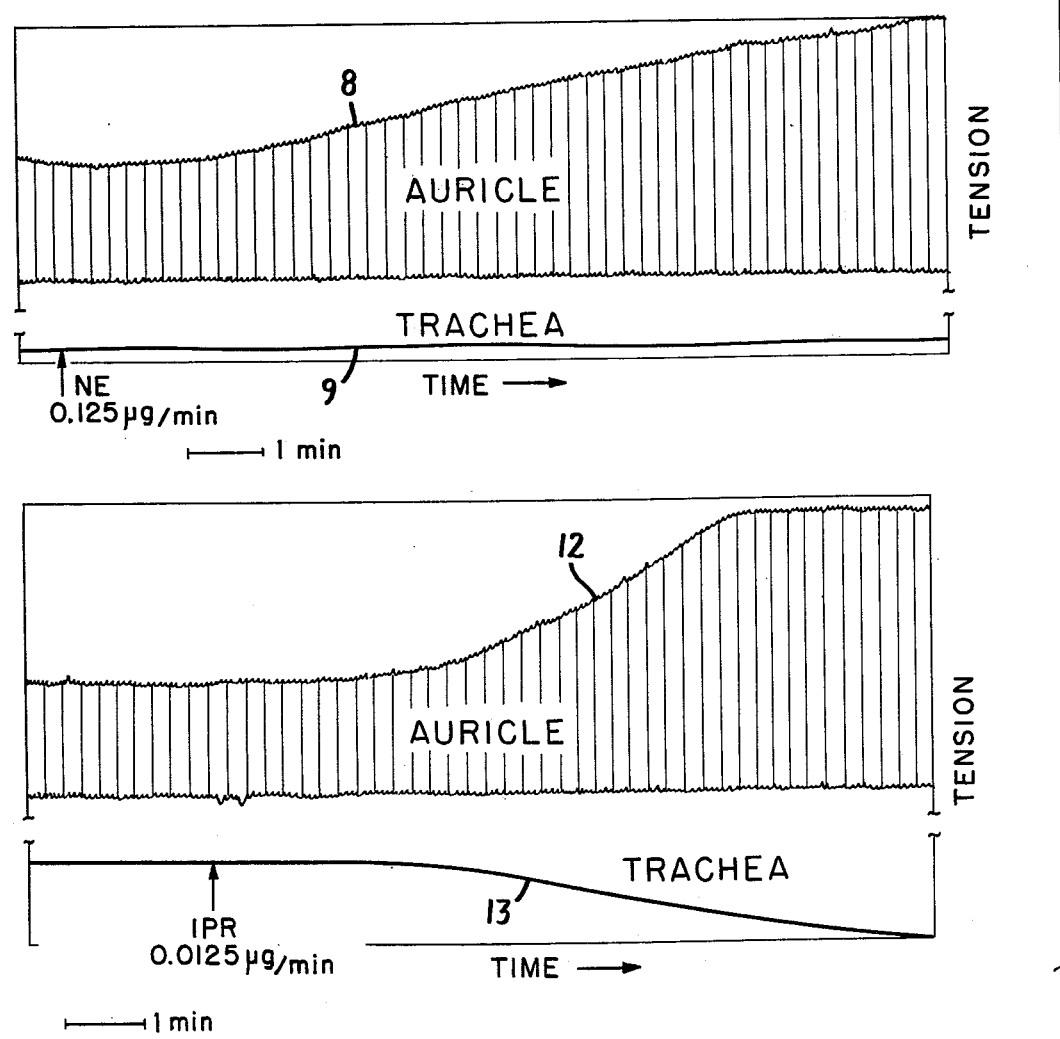
Figure 4:
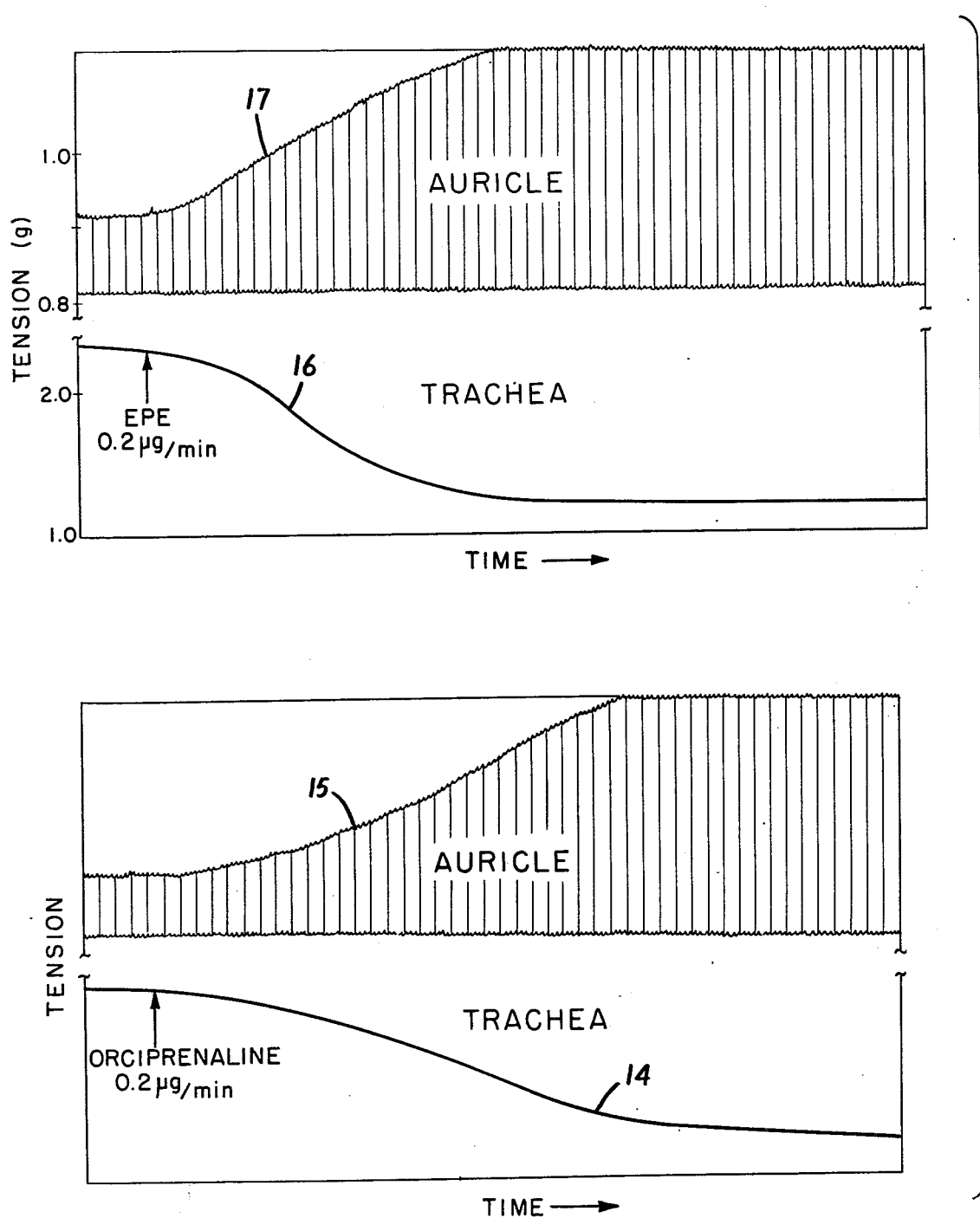
FIG. 4 shows the effect of epinephrine (EPE) and oriciprenaline on spirally cut trachea and right auricle from the guinea pig. Both preparations are dissected out from the same animal and run under identical experimental conditions.

Referring to FIG. 3, norepinephrine illustrates the behavior of a sympathomimetic amine which is a poor bronchodilator. It has a strong effect on the heart muscle (ref. no. 8) without affecting the bronchial muscles (ref. no. 9). In interpreting curves 8 and 9, reference should be made to the related control test on epinephrine for the auricle (ref. no. 10) and trachea (ref. no. 11) preparations. FIG. 3 also shows a test on this same preparation of the effect of isoprenaline (IPR) and FIG. 4 shows the effect of orciprenaline (ORC) on tracheal-auricle preparations. The effect of isoprenaline on the auricle (ref. no. 12) and trachea (ref. no. 13) are to be compared with the related control curves (ref. nos. 10 and 11) of FIG. 3, while the effect of orciprenaline on the trachea (ref. no. 14) and auricle (ref. no. 15) preparations are to be compared with the related control using epinephrine for that test, (ref. nos. 16 and 17). As can be seen from FIGS. 3 and 4, both isoprenaline and orciprenaline are strong cardiac stimulants in relation to their bronchodilator effect.

d. Effect on the heart – Langendorff preparation in vitro

The effect of the compound of the present invention was also studied in isolated rabbit heart (Langendorff preparation) the method used as described by Anden et al. (Acta Pharmacol. et Toxicol., 21 (1964) page 247). In this procedure, the isolated heart is mounted in a Krebs solution and the test compound is injected into it. Measurements are continuously recorded of the rate and force of contraction.

Figure 5:
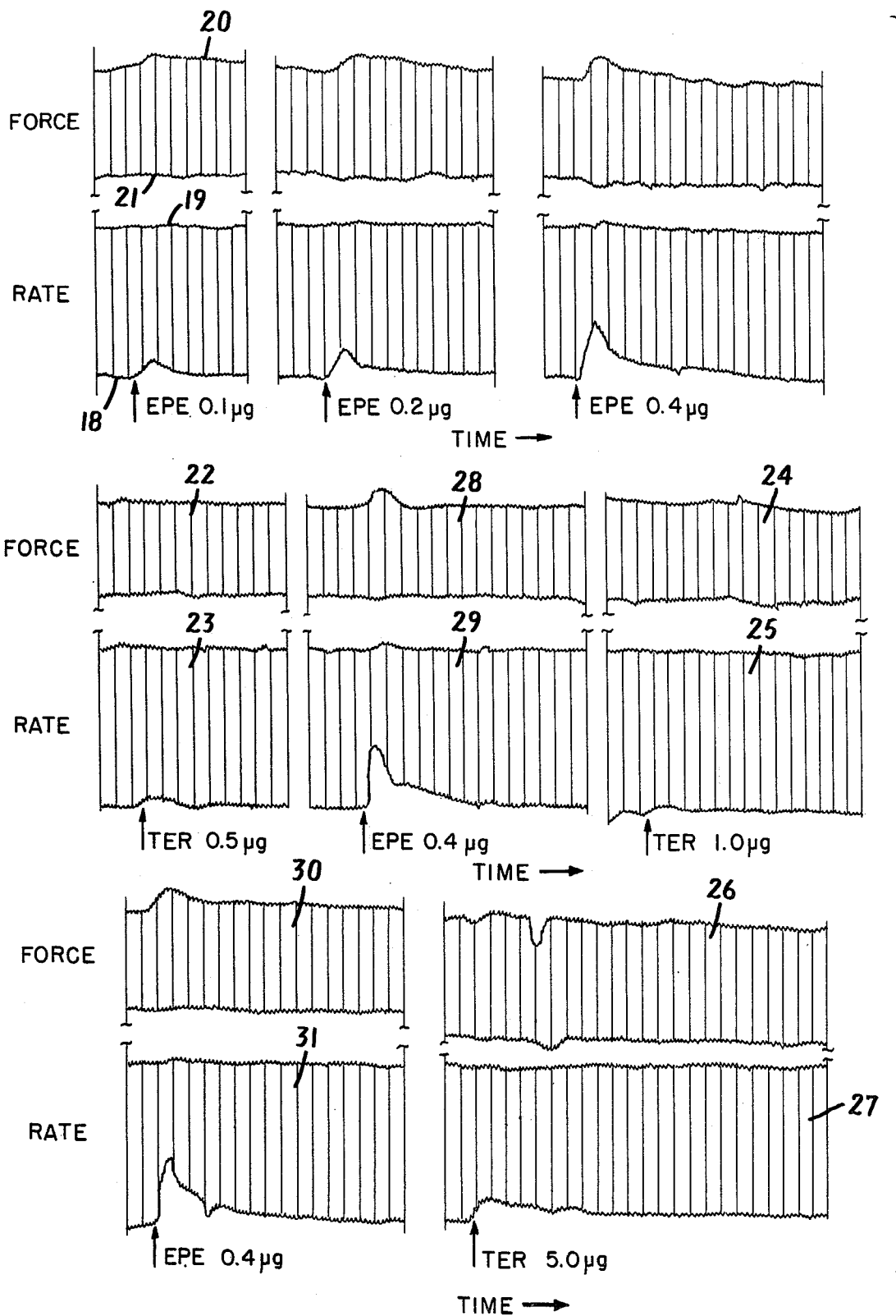
FIG. 5 illustrates the effect of epinephrine (EPE) and terbutaline on the rate and force of isolated rabbit heart.

The top portion of FIG. 5 displays the results of a first series of tests injecting epinephrine (EPE) at various concentrations. The tests using epinephrine establish a standard of comparison to evaluate subsequent test compounds in the same preparation. It is apparent that epinephrine causes an increase in the heart rate (ref. no. 18 of FIG. 5 upper) relative to the baseline therefor (ref. no. 19) and also an increase in the force of contraction (ref. no. 20) relative to the baseline of the force record (ref. no. 21). Increasing the amount of injected epinephrine to 0.2 micrograms and 0.4 micrograms increases both the chronotropic (rate) and inotropic effects (force) recorded.

The middle and lower portions of FIG. 5 show a comparison using this same test procedure of the effect on the heart lof terbutaline (TER) with the effect on the heart of epinephrine. It is apparent that the effect of terbutaline on the heart is weak (ref. nos. 22, 23, 24, 25, 26 and 27), while the effect of epinephrine is readily observable (ref. nos. 28, 29, 30 and 31).

It is estimated from these data that the effect of terbutaline on the isolated rabbit heart is only about 1/50 (one-fiftieth) of that of epinephrine.

Figure 6:
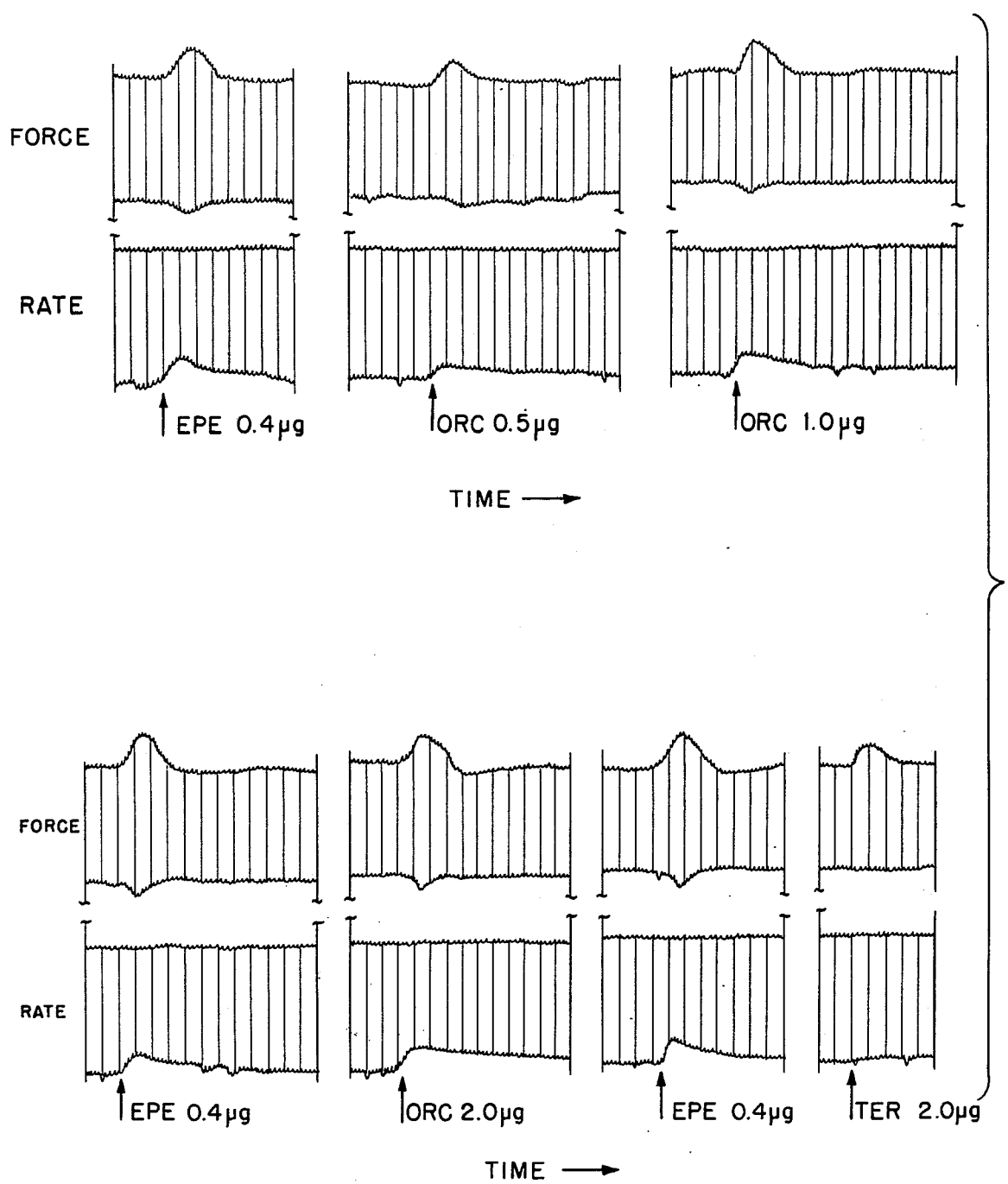
FIG. 6 illustrates the effect of epinephrine (EPE), orciprenaline and terbutaline on the rate and force of isolated rabbit heart.

The effect of orciprenaline (ORC) is compared with epinephrine and terbutaline in FIG. 6. The cardio-accelerating effect of orciprenaline shown in FIG. 6 is about one-fourth that of epinephrine and substantially more than the effect on the heart of terbutaline.

Employing this same procedure the cardiac stimulatory effect of 1-(3′,5′-dihydroxyphenyl)-2-(cyclobutylamino)-ethanol was measured. The test results showed that the effect on the heart of the cyclobutyl compound was less than 0.1 times that of epinephrine.

e. Effect on sphincter of Oddi

The effect of terbutaline on the choledochoduodenal sphincter of young, healthy cats was studied. Young animals weighing at least 2.0 kg were used. After being deprived of food but not water for 24 hours, they were anesthetized with pentobarbitol (40 mg/kg i.p.). The terminal portion of a common bile duct was isolated and cannulated toward the duodenum. The hepatic part of the bile duct was drained to prevent distention. The pressure was continuously recorded by the open tip technique. Details of the experimental set up have been published by Liedberg and Halabi [Acta. Chir. Scand. 136 (1970) page 208.] Heart rate was recorded in all experiments and blood pressure by arterial cannulation in some.

Figure 7:
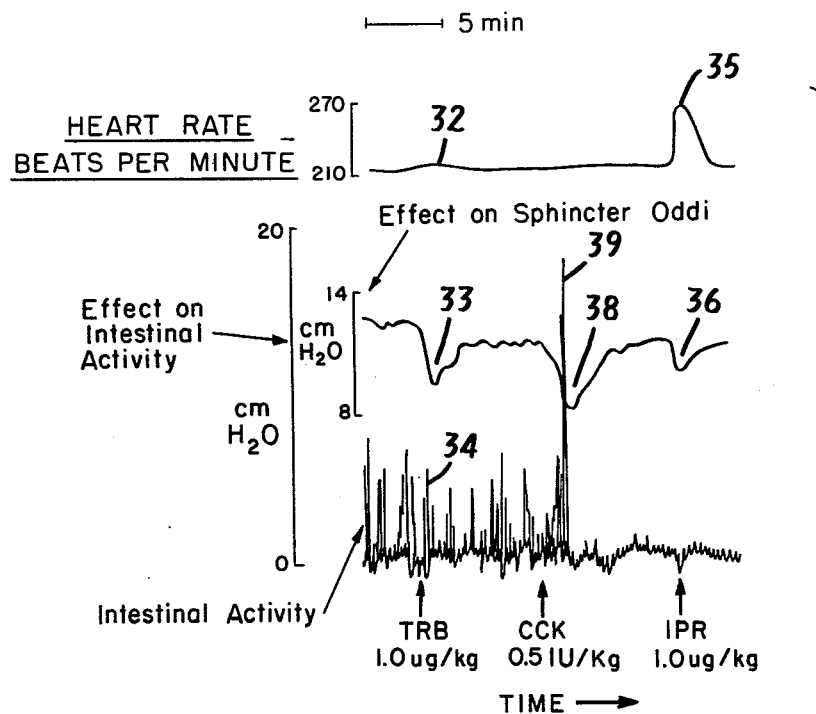
FIGS. 7 and 8 illustrate the effect of terbutaline on the sphincter of Oddi.
Figure 8:
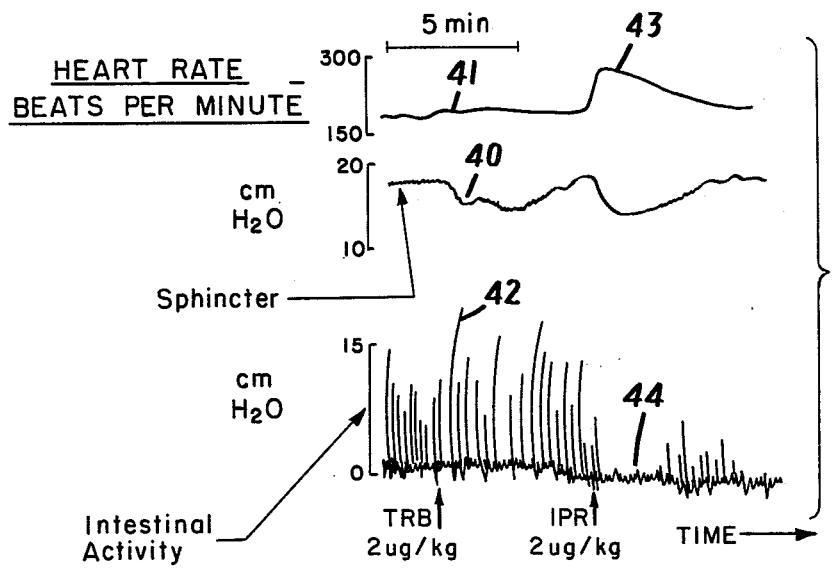

The effect of terbutaline and isoprenaline on bile duct pressure and duodenal pressure are graphically set forth in FIGS. 7 and 8. Referring to the upper curve of FIGS. 7 and 8, the heart rate is continuously recorded. Concurrent records are made in the middle curve and lower curve of the pressures measured respectively in the common bile duct and in the lower duodenum.

As shown in FIG. 7, injection of 1 μg/kg of terbutaline (TRB) substantially reduces the common bile duct pressures (ref. no. 33) but only slightly affects the heart rate (ref. no. 32) and the duodenal pressure (ref. no. 34) This shows that terbutaline relaxes the sphincter with minimum effect on the heart rate and duodenum. By contrast, isoprenaline, although it reduces common bile duct pressure (ref. no. 36); and thereby relaxes the sphincter, also produces marked tachycardia (ref. no. 35).

As a control in this test, the animal was also treated with 0.5 international units per kg of cholecysto kinin (CCK). CCK relaxed the sphincter (ref. no. 38) and markedly stimulated the duodenum (ref. no. 39).

In a second test of the effect of terbutaline and isoprenaline on the sphincter (see FIG. 8), the duodenal motility was measured without being affected by CCK. In the unstimulated sphincter a rhythmic activity independent on the duodenal motility is found. The i.v. injection of terbutaline relaxed the sphincter (ref. no. 40) with minimum effects on heart rate (ref. no. 41) and duodenum motility (ref. no. 42) whereas isoprenaline both produced tachycardia (ref. no. 43) and inhibited duodenal motility (ref. no. 44).

Of twenty-five cats, twenty responded in this way to terbutaline in the dose range 0.5–4.0 $\mu$g/kg; the other five responded similarly to 5–10 $\mu$g/kg. Isoprenaline in a dose of 0.5–5.0 $\mu$g/kg had a similar effect on the sphincter, but differed markedly from terbutaline in its effect on heart rate and intestinal activity.

C. Clinical Tests of Terbutaline

EXAMPLE 6.

Clinical Studies

Clinical studies have been made on the use of terbutaline in the treatment of asthmatic conditions. For control purposes in this study, the activity of the compound of the present invention was compared with orciprenaline.

All the patients were hospitalized for severe bronchial asthma. Before the patients were selected for the trial, spirometry was performed before and after isoprenaline inhalations to make sure that their obstruction was at least partly reversible by bronchodilating drugs. The tests were performed when the patients were in a relatively steady state of moderate asthmatic discomfort. Every morning during the trial control measurements of forced expiratory volume in one second ($FEV_{1.0}$) were made. These values had to be less than 70% of the predicted normal value taking in consideration sex, age and heights. All the patients were under treatment of different drugs for their asthma. Other bronchodilating drugs were withdrawn at least 6 hours before the start of the measurements. Most of the patients were treated with steroids, antibiotics and expectorants before the start of the trial. This regimen was continued unchanged during the trail period.

24 patients took part in the study, 10 male and 14 female. Average age was 51 years (range 15–71 years), mean body weight 64 kg (range 44–88 kg.) and height 166 cm (range 150–187 cm).

Methods

The trial was performed as a double blind study during three consecutive days with the patients serving as their own control. The drugs and doses used were terbutaline, 5.0 mg, and 7.5 mg and orciprenaline, 20 mg (Alupent)[1] Tablets containing 2.5 mg of terbutaline and placebo tablets with the same shape, color, etc. as these were used.[2] Only one dose of either terbutaline or orciprenaline was given each day. The patients always received four tablets, e.g. if the dose was 20 mg of orciprenaline, the patient got three placebo tablets with the same appearance as terbutaline 2.5 mg tablets and one Alupent tablets. The order of treatment was randomized according to the principle of Latin squares.

[1] Boehringer/Ingelheim Batch No. 80008 [2] Placebo tablets to Alupent were manufactured by AB Draco Lund, Sweden Lung function tests were made immediately before the administration of the tablets and after 1, 2, 3, 5 and 7 hours. $FEV_{1.0}$ was measured using a Vitalograph spirometer. The highest value of three measurements on each occasion was used in the calculations. All the patients had been trained to perform the tests the day before the start of the trail. After 3 and 7 hours, the patients were questioned for side effects. The same, specially trained, nurse assisted throughout the whole investigation.

The "Student's" t-test was used for statistical evaluation of the results. The degree of significance for the differences is given as almost significant ($p<0.05^{x}$) significant ($p<0.01^{xx}$) and highly significant ($p<0.001^{xxx}$).

Results

Figure 9:
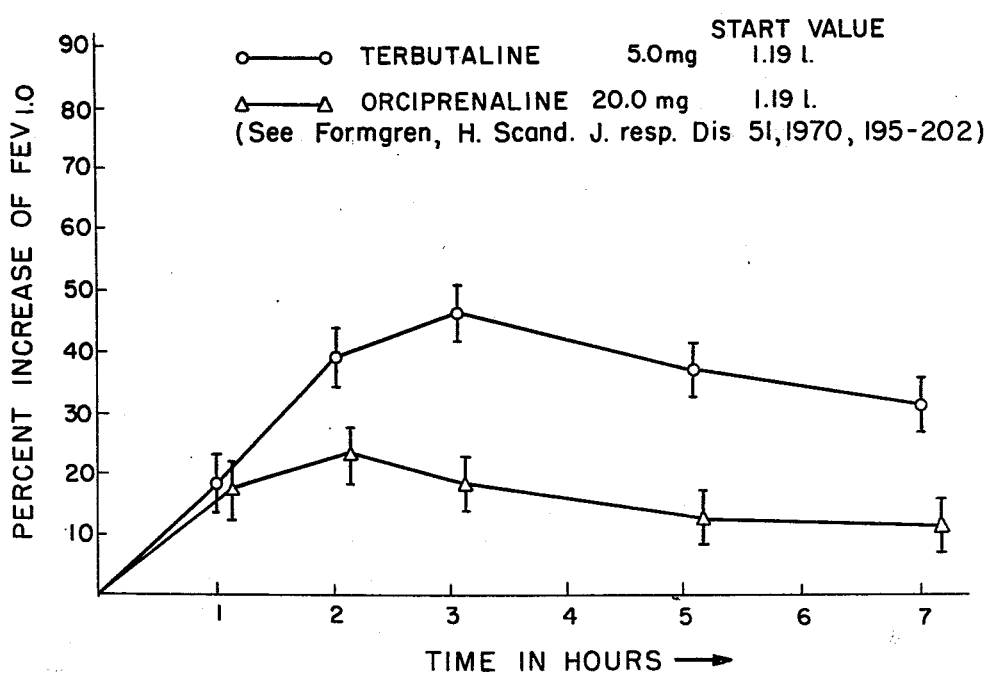
FIG. 9 illustrates the effect of terbutaline when used in the practical treatment of asthmatic patients.

The bronchodilating effect of the drugs expressed as changes in $FEV_{1.0}$ in percent of the starting values is illustrated graphically in FIG. 9. Both the drugs gave a clearcut increase of the spirometric values. However, the improvement obtained by terbutaline (5.0 mg/dose) was significantly greater than that of orciprenaline (20 mg/dose).

The duration of action also favored terbutaline. The maximal response obtained by orciprenaline occurred after 2 hours, at which time terbutaline showed better but not maximal effect. The maximum effect of terbutaline was reached after three hours.

The difference between terbutaline and orciprenaline regarding the changes of $FEV_{1.0}$ was statistically significant after 3 hours ($p<0.001$), 5 hours ($p<0.01$) and 7 hours ($p<0.05$).

Discussion

The study showed that orally given terbutaline was effective in relaxing bronchial obstruction in asthmatic patients. The duration of action was considerably longer and presumably longer than 5 hours. The results indicate that a dose of 5 mg of terbutaline was superior to 20 mg of orciprenaline, which does is recommended by the manufacturer with respect to both maximum effect and duration of effect.

The combination of pronounced broncholytic effect, negligible circulatory effects and a remarkably long duration of action makes it reasonable to expect that an oral dose of 5 mg of terbutaline administered 2–4 times a day, depending on the severity of the disease, is suitable for continuous daily use by patients with bronchial asthma. This statement applies not only to relaxation of acute bronchial obstruction, but also to the use as a prophylaxis against asthmatic attacks. Experiences from a study of the long term effects of oral terbutaline (5.0 mg 3 times daily) supports this expectation.

D. Laboratory tests of 1-(3',5'-dihydroxyphenyl)-2-cyclobutylamino ethanol

The pharmacological properties of 1-(3',5'-dihydroxyphenyl)-2-(cyclobutylamino)-ethanol of the present invention has been compared with 1-(3',4'-dihydroxyphenyl)-2-(cyclobutylamino)-ethanol. For identity, the compounds tested were assigned code numbers as follows:

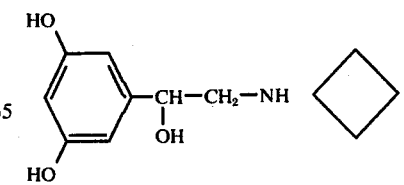

KWD 2025

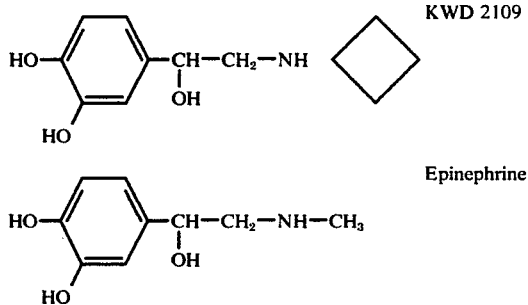

The tests, described in more detail below, compared KWD2025 (claimed in this application) with KWD2109 (described in the prior art). In some tests, KWD2025 and 2109 were compared with each other, and in other tests, these two compounds were each compared, in activity, to epinephrine, and the comparative activity of the two compounds was derived.

The object of these tests was to determine the selectively of bronchospasmolytic effect relative to the effect on the heart. For KWD2025 (of the present invention) and KWD2109 (of the prior art), this was done separately by measuring the effect on the bronchii and the heart in laboratory animals, both in vitro and in vivo. The results showed that KWD2109 was of greater overall activity than KWD2025; however, its activity in stimulating the heart was very much greater. Therefore, KWD2025 showed a substantial improvement in selectively as a bronchospasmolytic agent; or, in other words, in doses providing equal bronchospasmolytic activity, the effect on the heart of KWD2025 was materially reduced.

EXAMPLE 7.

a. Bronchospasmolytic effect in vitro

The trachea from a guinea pig was dissected out and spirally cut. It was mounted in a water-jacketed bath (37° C.) in Kreb's solution and aerated with oxygen (95%) and carbon dioxide (5%). Pilocarpine (1 μg/ml) was added. The load was about 2 g and the relaxation was recorded by means of a Grass force displacement transducer and a Grass polygraph model 5. The compound KWD2109 was tested on six preparations in which epinephrine was used as reference.

In this test, it was found that KWD2109 as a bronchospasmolytic agent was 14 times as effective as KWD2025. KWD2109 was 8.6 ± 1.7 times as effective as epinephrine in six tests.

TABLE 1

| | Isolated guinea pig trachea. Effect of KWD2109 compared with Epinephrine and KWD2025 | | |
|---|---|---|---|
| Compound | Effect x Epinephrine | Number of Experiments | Effect x KWD2025 |
| KWD2109 | 8.6 ± 1.7 | 6 | 14 | b. Bronchospasmolytic effect in anesthetized cat

Cats of both sexes (2.5 – 4 kg) were initially anesthetized with Nembutal 35 mg/kg intraperitoneally. Bronchospasmolytic effect was recorded according to Konzett & Rossler. Bronchoconstriction was produced by intravenous injections of histamine into the jugular vein. The drug was injected by the same route 3 minutes before the injection of histamine. Overflow was recorded by means of a Grass volume transducer. Changes in arterial mean pressure and heart rate were continuously recorded on a Grass polygraph. KWD2109 was used as a reference. Heart rate and arterial mean pressure were continuously recorded during the experiment. Three cats were used.

The bronchospasmolytic effect of KWD2109, by the Konzett & Rossler procedure was 7.2 times the activity of KWD2025.

c. Protecting effect against histamine aerosol in intact guinea pigs

The compound KWD2109 and KWD2025 have been compared in preventing bronchospasm induced by histamine aerosol in guinea pigs.

The drug was injected intraperitoneally 15 minutes (Table 2) or administered orally 30 minutes (Table 3) before histamine treatment. The dose of the drugs protecting 50 percent of the animals for more than 4 minutes is denoted "ED50". In untreated animals only 1–2 percent will withstand the histamine aerosol for more than 4 minutes.

To study the duration of the effect, 2 mg/kg was administered orally to intact guinea pigs at different time intervals before the histamine treatment. Two series each including eleven groups of 6 animals was studied. The groups were tested in histamine aerosol 10, 20, 30, 40, 50, 60, 120, 180, 240, 300 and 360 minutes after the administration of the compound. The percent of animals in each group protected more than 4 minutes and more than 10 minutes was determined.

The results are given in Tables 2 and 3. After intraperitoneal administration, KWD2109 is 3.5 times as active as KWD2025 (i.e. 3.5 times as much KWD2025 was required to produce the effect KWD2109). The test was repeated using orally administered drugs. By the oral route, KWD2109 was 3.1 times as active as KWD2025.

TABLE 2

| Intact guinea pigs treated by histamine-aerosol 15 minutes after i.p. administration of drugs | | |
|---|---|---|
| Compound | ED50 mg/kg m ± s.e. | No. of animals |
| KWD2109 | 0.17 ± 0.02 | 40 |
| KWD2025 | 0.60 ± 0.07 | 40 | s.e. (standard error) according to Miller and Tainter Proc. Soc. Exp. Biol. 57,261, 1944.

TABLE 3

| Intact guinea pigs treated by histamine-aerosol 30 minutes after peroral administration of drugs | | |
|---|---|---|
| Compound | ED50 mg/kg m ± s.e. | No. of animals |
| KWD2109 | 0.55 ± 0.14 | 40 |
| KWD2025 | 1.7 ± 0.3 | 40 | s.e. (standard error) according to Miller and Tainter Proc. Soc. Exp. Biol. 57,261, 1944.

d. Effect on isolated guinea pig heart

The isolated guinea pig heart was perfused according to Langendorff. The method used is described by Anden et al. (Acta. Pharmacol. et Toxicol. 21, 247, (1964). Contractions in the heart were recorded by means of a force displacment transducer and a Grass polygraph Model 7. Epinephrine was used as reference.

KWD2109 and KWD2025 were tested on the same preparation. The comparisons of effects were based on dose for 50 percent increase in chronotropic effect and 10 percent increase in inotropic effect.

The results are given in Tables 4 and 5

TABLE 4

Isolated guinea pig heart. Effect of KWD2109 on heart rate. Comparison is made with KWD2025 and epinephrine

| Compound | Effect x Epinephrine | Number of Experiments | Effect x KWD2025 |
|---|---|---|---|
| KWD2109 | 11.8 ± 6.5 | 3 | 168 |

TABLE 5

Isolated guinea pig heart. Effect on force. Comparison is made with KWD2025 and epinephrine

| Compound | Effect x epinephrine | Number of Experiments | Effect x KWD2025 |
|---|---|---|---|
| KWD2109 | 5.5 ± 3.2 | 3 | 79 |

Comparison of the test results from Examples 7a to 7d shows that KWD 2109 is between 3 and 7 times more active as a bronchospasmolytic agent than KWD 2025; however, the effect on the heart of KWD 2109 is in the order of 80 to 160 times the effect of KWD 2025. Thus, when used in equal bronchospasmolytic doses, KWD 2025 provides a substantially reduced effect on the heart.

This conclusion is confirmed by simultaneous tests of the effect on KWD 2025 and KWD 2109 on the heart and bronchii in the following laboratory test:

EXAMPLE 8.

Direct comparison of heart muscle and tracheal muscle effects.

a. Effect on isolated guinea pig auricle and trachea

The left auricle was dissected out and mounted together with spirally-cut trachea from the same animal in a 100 ml bath in Kreb's solution (37° C.) well aereated with a mixture of oxygen (95%) and carbon dioxide (5%). The auricle was electrically stimulated with square wave pulses from a Techtronic Stimulator (voltage 2–4; duration: 10 m sec; frequency 1 per second). This is, in general, the same procedure described above in Example 5c. By conducting the tests of the two organs in the identical bath and under identical experimental conditions it is possible to demonstrate directly that KWD2025, in a dose sufficient to produce an effect on the trachea, has a materially reduced effect on the auricle.

Using the dual bath preparation, tests were made of the effect on the trachea and auricle of KWD2025 (of the present invention) and of the known drugs KWD2109 and epinephrine. The drug to be tested was added to the bath in the predetermined amount and allowed to act upon the organs for ten minutes.

The bronchospasmolytic effect of KWD2109 was 8 to 10 times the effect of epinephrine (measured) as the relative amounts of test compound required to produce an equal effect). When doses of KWD2109 and epinephrine that produced the same effect on the trachea were compared, the effect of KWD2109 on the auricle was of the same order as that of epinephrine.

The bronchospasmolytic effect of KWD2025 was 0.8 and 0.9 times the effect of epinephrine when doses of KWD2025 and epinephrine producing the same effect on the trachea were compared the effect on KWD 2025 on the auricle (inotropic effect) was only 0.1 to 0.33 times the effect of epinephrine.

b. Tests on anesthetized cat

The relative bronchospasmolytic and cardiovascular effects of compounds can be tested in the method of Konzett & Rossler (see Example 5b above). As has already been described, the test animal is force-ventilated and the effect of various compounds in controlling histamine-induced bronchoconstriction, as reflected by overflow of the forced ventilation in excess of lung capacity, is used as a measure of the bronchospasmolytic effect. Concurrently in the same animal, changes in heart rate and arterial mean pressure can be simultaneously recorded.

In carrying out this procedure, broncho-constriction in the test animal is induced by injection of histamine. The ability of KWD2025 and KWD2109 to control the histamine-induced bronchoconstriction is measured by injecting the test compound three minutes before injection of histamine. During the three minutes after injection of the test compound, and before injection of histamine, the effect of the test compound on the heart rate is recorded.

The results of this test showed that in equal bronchospasmolytically effective doses, KWD2109 had a more pronounced effect on the heart rate than did KWD2025.

Summary of Tests on KWD2025 in Examples 7 and 8

From the test results given above it is seen that KWD2109 shows an in vitro bronchospasmolytic acitivity which is about 14 times better than that of KWD2025 (Example 7a). In the in vivo tests or guinea pig bronchospasmolytic activity KWD2109 has an effect which is about 3 times that of KWD2025 after intraperitoneal and oral administration (Example 7c). After intravenous injection in cats, the bronchospasmolytic effect of KWD2109 is about 7 times that of KWD2025 (Example 7b). These differences in bronchospasmolytic effect obtained in the different tests probably are due to a more rapid inactivation of KWD2109 compared with that of KWD2025.

KWD2109, however, has an in vitro chronotropic effect on the heart rate which is about 170 times greater than that of KWD2025, and KWD2109 has a positive inotropic effect on the heart which is about 80 times that of KWD2025 (Example 7d). Thus, in terms of therapeutic index for bronchospasmolytic effect over the effect on the heart and giving KWD2025 the index 1.0, KWD2109 has the value of 0.083 when the inotropic heart effect is considered. It is evident that while KWD2109 exhibits a greater bronchospasmolytic activity than KWD2025 in the in vitro tests, the pronounced effect on the heart of KWD2109 as compared with KWD2025 is a great drawback.

The pronounced effect of KWD2109 on the heart as compared with KWD2025 was verified in the in vitro study on isolated guinea pig auricle and trachea when mounted in the same bath, where it was shown that KWD2109 increased the force of contraction in the auricle in concentrations where it relaxed the trachea, while KWD2025 relaxed the trachea without affecting the auricle [Example 8a].

The highly selective effect on the bronchial muscles which is exhibited by KWD2025 makes KWD2025 a bronchospasmolytic agent which is clearly superior to the previously known compound KWD2109.

E. Toxicity Tests

EXAMPLE 9.

Toxicity tests

The toxicity of a racemic mixture of terbutaline for mice after i.v., s.c. and oral administration is given in Table 6. For comparison corresponding $LD_{50}$ values are given for orciprenaline.

TABLE 6

| Compound | Adm. | Acute toxicity in mice $LD_{50}$ mg/kg mice (base) | Number of animals |
|---|---|---|---|
| Terbutaline | i.v. | 47 | 25 |
| Terbutaline | s.c. | 240 | 25 |
| Terbutaline | oral | 3200 | 20 |
| Orciprenaline | i.v. | 80 | 25 |
| Orciprenaline | s.c. | 295 | 25 |
| Orciprenaline | oral | 4800* | — |

*According to Engelhart et al.;Arzneimittelforschung 11, (1961), 521–525

Toxicity measurements on the cyclobutyl compounds of the present invention shows an $LD_{50}$ for KWD2025 [1-(3',5'-dihydroxyphenyl)-2-(cyclobutylamino)-ethanol) after i.v. administration in mice is 54 mg/kg body weight.

The compounds of the present invention have a very favorable ratio of cardiac stimulation to bronchospasmolytic activity. This unexpected property makes them particularly suitable for treatment of bronchospastic conditions, such as asthma and other related ailments affecting the respiratory system.

F. Optical Isomers

The compounds of the present invention, as is apparent from their structure, are optically active. They can be resolved in the usual manner, as illustrated by the following example:

EXAMPLE 10.

Optical resolution of 1-(3',5'-dihydroxyphenyl)-2-(benzyl-t-butylamino)-ethanol.

a. Optical resolution of 1-3',5'-dibenzyloxy-phenyl-2-(benzyl-t-butylamino)-ethanol 25.0 g of 1-(3'15'-dibenzyloxphenyl)-2-(benzyl-t-butylamino)-ethanol (racemic base) were dissolved in 375 ml of methanol under heating and 19.0 g of (-)dibenzoyl-tartaric acid in 125 ml of methanol were added. The mixture was refluxed for 30 minutes. After evaporation an oil was recovered. This was dissolved in boiling isopropanol and water was added until turbidity appeared and then a few ml of isopropanol to get a clear solution. The solution was left over night to crystallize and 37.0 g of a white crystalline product was isolated. Another 7.0 g were recovered from the filtrate after reduction of the volume. The two fractions were mixed and dissolved in 1100 ml of absolute ethanol, filtered and allowed to crystallize. This product was recrystallized from absolute ethanol until the rotation remained constant (6 times $[\alpha]_D^{20} = -34.2°$ (1% in absolute methanol). Yield 4.5 g.

b. Preparation of (−)-1-(3',5'-dihydroxyphenyl)-2-(t-butylamino)-ethanol hydrobromide 4.0 g of the product of part (a) were suspended in water, ether was added and then aqueous ammonia. The extraction of the base was performed with two portions of ether. Diluted hydrobromic acid was added to the ether phase and stirred for 1.5 hours. A white crystalline product was formed. This was filtered off and washed with water and dry ether. Yield 2.8 g $[\alpha]_D^{20} = +$ (1% in absolute methanol).

This product was dissolved in 75 ml of absolute ethanol and 0.15 g of 10% palladium charcoal were added and the hydrogenation performed at room temperature for four hours at five atmospheres pressure. The catalyst was filtered off and the residue evaporated to dryness. A small amount of ethanol was added to dissolve the product and then ether was added until turbidity was observed. The crystalline precipitate which separated after standing, was filtered off with suction and was dried for seven hours (over boiling toluene) Yield 1.2 g.

$Br^-$(calculated) = 26.1% $Br^-$(found) = 25.8% $[\alpha]_D^{20} = -34.6°$ (1% in absolute methanol) M.p. 241°–242° C.

c. Preparation of (+)-1-(3',5'-dihydroxyphenyl)-2-(t-butylamino)-ethanol hydrobromide 23.7 -dibenzyloxyphenyl)-g base of 1-(3',5'-dibenxyloxphenyl)-2-(benzyl-t-butylamino)-ethanol, derived from the collected supernatant solutions from the peparation of the (-)-1-(3',5'-dibenzyloxphenyl)-2-(benzyl-t-butylamino)-ethanol, were dissolved in 250 ml of methanol and 18.2 g of (+)-dibenzoyl-tartaric acid in 250 ml of methanol were boiled under reflux for 60 minutes. The product was then worked up in the same way as described above and recrystallized from absolute ethanol (twice) $[\alpha]_D^{20} = +34.3°$ (1% in absolute methanol). Yield 10.5 g.

The hydrobromide was made from 9.5 g of this salt in the same way as described above. Yield 6.2 g $[\alpha]_D^{20} = -33.0°$ (1% in absolute methanol). The hydrogenation of 5.5 g of this product was performed as earlier described. It was crystallized from ethanol/ether. Yield 2.7 g $[\alpha]_D^{20} = +34.2°$ (1% in absolute methanol).

$Br^-$(calculated) = 26.1% $Br^-$(found) = 25.8% M.P. 241°–243° C.

G. Preparation of Diacyloxy Phenyl Compounds

While the compounds of the present invention are conveniently used in the feee dihydroxy form, they may also be used in the form of the dialkanoyl esters. Illustrative acyloxy groupings which may be substituted for the hydroxy phenyl groups are:

$$CH_3\overset{O}{\underset{\|}{C}}-O-$$

$$CH_3-CH_2-\overset{O}{\underset{\|}{C}}-O-$$

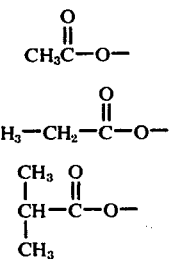

and

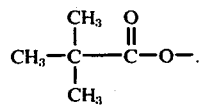

The preparation and use of the esters is illustrated by the following examples:

EXAMPLE 11.

Preparation of 1-(3',5'-diacetoxyphenyl)-2-(t-butylamino)-ethanol a. Preparation of 3,5-dihydroxy-ω-(t-butylamino)-acetophenone hydrobromide 27.0 g of 3,5-dibenzyloxy-ω-(benzyl-t-butylamino)-acetophenone hydrobromide were dissolved in 400 ml of glacial acetic acid and hydrogenated at atmospheric pressure and room temperature in the presence of 3.0 g of 10% palladium charcoal. When the calculated amount of hydrogen was taken up the hydrogenation was stopped. Absolute ethanol was added to dissolve the formed crystalline product. The catalyst was filtered off and the volume of the filtrate was reduced by evaporation until crystallization started. Yield 20.0 g.

b. Preparation of 3,5-diacetoxy-ω-(t-butylamino) acetophenone hydrobromide 3.0 g of 3,5-dihydroxy-ω-(t-butylamino)-acetophenone hydrobromide were refluxed under stirring with 2.5 g of acetic anhydride in 75 ml of glacial acetic acid under nitrogen atmosphere for 16 hours. The solvent was evaporated and the residue dissolved in ethanol. The addition of absolute ether, crystallized the product, 3,5-diacetoxy-ω-(t-butylamino)-acetophenone hydrobromide. It was recrystallized from methanol/ether. Yield 2.0 g M.p. 191°–193° C.

c. Preparation of 1-(3',5'-diacetoxyphenyl)-2-(t-butylamino)-ethanol hydrobromide 1.0 g of 3,5-diacetoxy-ω-(t-butylamino)-acetophenone hydrobromide was dissolved in absolute ethanol and hydrogenated in a Parr pressure reaction apparatus at 50° C and 5 atmospheres pressure for 17 hours in the presence of 0.1 g of 10% palladium charcoal. The catalyst was filtered off and the volume of the filtrate was reduced be evaporation. By the addition of absolute ether, the hydrobromide of 1-(3',5'-diacetoxyphenyl)-2-(t-butylamino)-ethanol crystallized.
Yield 0.7 g. M.p. 108°–111° C.

The compounds 1-(3',5'-diisobutyryloxyphenyl)-2-(t-butylamino)-ethanol hydrobromide (M.p. 168°–170° C.), 1-(3',5'-dipropionyloxyphenyl)-2-(t-butylamino)-ethanol hydrobromide (M.p. 114°–116° C.) were prepared according to the same method as described for the preparation of 1-(3',5'-diacetoxphenyl)-2-(t-butylamino)-ethanol hydrobromide.

EXAMPLE 12.

Preparation of 1-(3',5'-dipivaloyloxphenyl)-2-(t-butylamino)-ethanol.

a. Preparation of 3,5-dipivaloyloxy-ω-(benzyl-t-butylamino)-acetophenone hydrobromide To 16.0 g of 3,5-dipivaloyloxy-ω-bromoacetophenone in 200 ml of dry benzene were added 22.0 g of benzyl-t-butylamine. The reaction mixture was refluxed for four hours and then allowed to stand at room temperature for 15 hours. The benzene phase was evaporated to dryness and absolute ether was added. Benzyl-t-butylamine hydrobromide crystallized out and was filtered off. 50 ml of 10% hydrobromic acid were added to the filtrate under stirring and a crystalline product of 3,5-dipivaloyloxy-ω-(benzyl-t-butylamino)-acetophenone hydrobromide was formed.
Yield 11.0 g M.p. 162°–167° C.

b. Preparation of 1-(3',5'-dipivaloyloxyphenyl)-2-(t-butylamino)-ethanol hydrobromide 3.0 g of 3,5-dipivaloyloxy-ω-(benzyl-t-butylamino)-acetophenone hydrobromide were dissolved in absolute ethanol and hydrogenated in a Parr pressure reaction apparatus for 20 hours at 50° C. and five atmospheres pressure in the presence of 0.3 g of 10% palladium charcoal. The catalyst was filtered off and the filtrate evaporated to dryness. The residue was crystallized from chloroform/ether/petroleum ether. (B.p. 60°–85° C.).
Yield 1.8 g M.p. 190°–192° C.

H. Pharmacological Tests On 1-(3',5'-diacyloxyphenyl)-2-aminoethanols

As in examples 7 and 8, the objective is to ascertain the selectivity as a bronchospasmolytic agent, relative to cardiac effects, shown by the test compounds.

The compounds evaluated are referred to by code numbers and structural formulas noted below. The comparisons made are based on weight basis unless otherwise stated.

| Code | Structural Formula |
|---|---|
| KWD2037 | 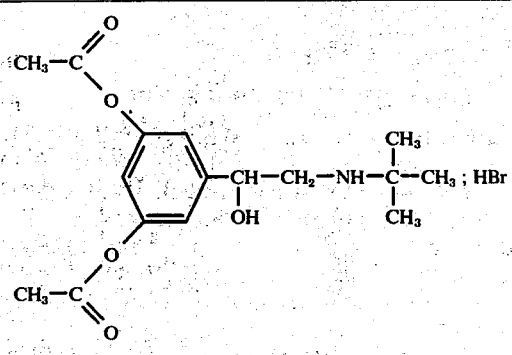 |

-continued

| Code | Structural Formula |
|------|--------------------|
| KWD2057 | (structure) |
| KWD2058 | (structure) |
| KWD2085 | (structure) |

For purposes of comparison, terbutaline was used in a number of the following tests. Terbutaline has the formula:

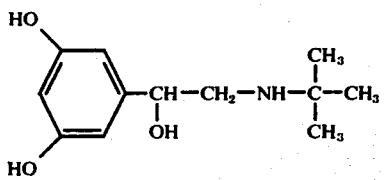

EXAMPLE 13.

Bronchospasmolytic effect in vitro

The trachea from a guinea pig was dissected out and spirally cut. It was mounted in a water-jacketed bath (37° C.) in Krebs solution and aerated with oxygen (95%) and carbon dioxide (5%). Pilocarpine (2 μg/ml) was added. The load was adjusted to about 2 g and relaxations in the trachea were recorded by means of a Grass force displacement transducer and a Grass polygraph model 5 (see Example 5 above). The cumulative method was used (-)-Epinephrine was used as reference. The comparisons presented in Table 7 are based on $ED_{50}$ -values.

Table 7

| Substance | Bronchospasmolytic effect x (−) epinephrine | Number of Experiments |
|-----------|---------------------------------------------|----------------------|
| Terbutaline | 0.8 ± 0.1 | 10 |
| KWD2037 | 0.7 | 3 |
| KWD2057 | 0.4 | 1 |
| KWD2058 | 0.6 ± 0.2 | 3 |

EXAMPLE 14.

Bronchospasmolytic effect in the anesthetized cat.

Bronchospasmolytic effect was studied according to the method of Konzett & Rossler (see Example 5b above). Bronchospasm was induced by i.v. injections of histamine into the left jugular vein. Overflow was recorded by means of a Grass volume transducer and a Grass polygraph model 5. changes in arterial mean pressure and heart rate, were continuously recorded during the experiment. Terbutaline was used as reference in all experiments. The comparisons are based on $ED_{50}$ -values. The results are given in Table 8.

TABLE 8

| Substance | Bronchospasmolytic effect x Terbutaline | Number of Experiments |
|---|---|---|
| KWD2037 | 0.7 ± 0.1 | 2 |
| KWD2057 | 0.5 | 1 |
| KWD2058 | 1.0 ± 0.1 | 3 |

EXAMPLE 15.

Protecting effect against histamine aerosol in guinea pigs

Male guinea pigs (200–300 g) were used. Bronchoconstriction was produced by letting the animals inhale a histamine aerosol. The histamine (0.4 mg base/ml) was nebulized under standard conditions with two devices according to Rooth and Peterson (Acta. Med. Scand. Supplement 228, 1 (1949). In these experiments, the end point for the exposure of the animals in the aerosol was the observation of a sudden decrease of the respiratory frequency. Each test substance was injected intraperitoneally 15 minutes (40 animals) or administered orally 30 minutes (40 animals) before histamine treatment. The dose protecting 50 percent of the animals for more than 4 minutes is denoted $ED_{50}$. (See Table 9) In untreated material only 1 – 2 percent will withstand the histamine aerosol for more than 4 minutes.

TABLE 9

| Substance | ED 50 (mg/kg) i.p. adm. | ED 50 (mg/kg) oral adm. |
|---|---|---|
| Terbutaline | 0.15 | 0.4 |
| KWD2037 | 0.7 | 0.4 |
| KWD2057 | 0.2 | 1.0 |
| KWD2058 | 1.0 | 0.15 |
| KWD2085 | 0.13 | 0.24 |

All the esters tested but KWD2085 are somewhat less effective than terbutaline in protecting the guinea pigs to withstand the histamine aerosols after i.p. administration. After oral administration, however, the esters are equal or more effective than terbutaline with the exception of KWD2057. The di-isobutyric ester (KWD2058) is 2.5 times more effective than terbutaline after oral administration.

EXAMPLE 16.

Effect on isolated heart from guinea pig.

The isolated guinea pig heart was perfused according to Langerdorff. The method used in described by Anden et al. [Acta Pharmacol. et Toxicol. 21, 247, (1964)]. Contractions in the heart were recorded by a force displacement transducer and a Grass polygraph model 5. The recovery of the heart was tested with (−) epinephrine between every dose of the substance tested. Terbutaline was used as reference. The results are given in Table 10.

TABLE 10

| Substance | Effect on heart rate x terbutaline | Effect on force of contraction x terbutaline | No. of Experiments |
|---|---|---|---|
| KWD2037 | 0.05 ± 0.01 | 0.03 ± 0.01 | 4 |
| KWD2057 | 0.06 | 0.00 | 2 |
| KWD2058 | 0.00 | 0.00 | 2 |

The common feature of all esters tested is that they per se have no direct effect on the heart muscle, but that they, due to hydrolysis, cause a weak effect. With KWD2058 no effect was obtained on the heart rate in doses up to 100 μg.

EXAMPLE 17.

Haemodynamic studies.

The haemodynamic effects of KWD2058 and terbutaline were studied in anesthetized cats after i.v. injection in the left femoral vein. Three experiments were done. The effects on arterial mean pressure, pulse pressure (right carotid artery) and heart rate were recorded.

To study the effect of the compounds on the peripheral vascular resistance, constant flow was arranged in the right hind limb on two cats by means of a Sigma motor pump connected to arteria femoralis. Injections were made intra-arterially and variations in the peripheral resistance were recorded as pressure changes. The results are given in Table 11.

TABLE 11

| Arterial mean pressure | (0.4 ± 0.1) × terbutaline |
| Pulse rate | (0.4 ± 0.1) × terbutaline |
| Heart rate | (0.4 ± 0.1) × terbutaline |
| Change in peripheral resistance | (0.4 ± 0.1) × terbutaline |

EXAMPLE 18.

Toxicity study in mice.

The toxicity was studied in mice (NMRI, male, 18-28 g) 24 hours after i.v. and oral administration. The animals were observed during 5 days. No further deaths occurred. The results are given in Table 12.

TABLE 12

| Compound | Adm. | LD 50 + Standard error | Number of animals |
|---|---|---|---|
| Terbutaline | i.v. | 52 ± 3 | 50 |
| | p.o. | 3200 | 20 |
| KWD2037 | i.v. | 112 ± 5 | 50 |
| | p.o. | 2100 | 40 |
| KWD2057 | i.v. | 70 ± 4 | 60 |
| | p.o. | 2200 | 40 |
| KWD2058 | i.v. | 52 ± 4 | 50 |
| | p.o. | 2150 | 50 |
| KWD2085 | i.v. | 23 + 2 | 50 |
| | p.o. | 2200 | 40 |

Discussion on Tests on Diesters, Examples 13-18

The compounds KWD2037, KWD2057, KWD2058 and KWD 2085 have per se weaker bronchospasmolytic effect in vitro than terbutaline, and much less direct heart effect than terbutaline. In vivo, where the esters are enzymatically hydrolyzed to terbutaline, the bronchospasmolytic effect in anesthetized cat (after i.v. administration) is about the same as that of terbutaline. Haemodynamic studies in cat reveal that the effect of KWD2058 on arterial means pressure, pulse pressure, heart rate and peripheral vascular resistance is about half of that of terbutaline. All the esters show good effect in protecting intact guinea pigs from a histamine aerosol after i.p. administration as well as after p.o. administration.

These data show, therefore, that the diesters of terbutaline show generally at least as much selectivity in bronchospasmolytic effect relative to cardiovascular effects as terbutaline.

The compounds KWD2037, KWD2057, KWD2058 and KWD2085 exhibit an improved oral absorption in comparison with terbutaline as is indicated by their higher oral toxicity. The compound KWD2058 shows a particularly good oral absorption in comparison with terbutaline as is seen in the $ED_{50}$ test result at oral administration in Table 9.

I. Pharmaceutical Compositions

The following examples illustrate how the compounds of the instant invention can be incorporated in pharmaceutical compositions:

EXAMPLE 19.

Aerosol for inhalation

| | |
|---|---|
| Active substance | 1.00 g |
| Miglyol | 0.20 g |
| Frigen 11/12/113/114 | ad 100.0 g |

EXAMPLE 20.

Tablets

Each tablet contains:

| | |
|---|---|
| Active substance | 5.0 mg |
| Maize starch | 25.0 mg |
| Lactose | 205.0 mg |
| Gelatin | 1.5 mg |
| Talc | 12.0 mg |
| Magnesium stearate | 1.5 mg |
| | 250.0 mg |

EXAMPLE 21.

Suppositories

| | |
|---|---|
| Each suppository contains: | |
| Active substance | 5.0 mg |
| Ascorbyl palmitate | 1.0 mg |
| Suppository base (Imhausen II) | ad 2,000.0 mg |

EXAMPLE 22.

Syrup

| | |
|---|---|
| Active Substance | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified color | 0.015 g |
| Purified water | ad 100.0 g |

EXAMPLE 23.

Injection solution

| | |
|---|---|
| Active substance | 0.500 mg |
| Sodium pyrosulfite | 0.500 mg |
| Disodium edetate | 0.100 mg |
| Sodium chloride | 8.500 mg |
| Sterile water for injection | ad 1.00 ml |

EXAMPLE 24.

Inhalation solution

| | |
|---|---|
| Active substance | 5.00 g |
| Sodium pyrosulfite | 0.10 g |
| Disodium edetate | 0.10 g |
| Purified water | ad 100.0 ml |

EXAMPLE 25.

Solution for rectal administration (Rectal Vials)

| | |
|---|---|
| Active substance | 5.0 mg |
| Sodium pyrosulfite | 1.5 mg |
| Disodium edetate | 0.3 mg |
| Sterile water | ad 3.0 ml |

EXAMPLE 26.

Sublingual tablets

| | |
|---|---|
| Each tablet contains: | |
| Active substance | 5.00 mg |
| Lactose | 85.00 mg |
| Agar | 5.00 mg |
| Talc | 5.00 mg |
| | 100.00 mg |

EXAMPLE 27.

Drops

| | |
|---|---|
| Active substance | 2.00 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.00 ml |

We claim:
1. A compound effective for producing bronchial dilation in animals, including humans, selected from the group consisting of
   i. ethanol amines having the formulas

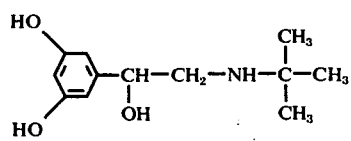

and

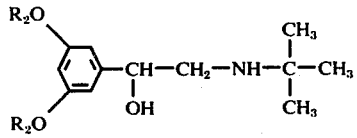

wherein $R_2$ is the acyl radical of a 2-5 carbon fatty acid and
ii. pharmaceutically acceptable salts thereof.
2. The compound according to claim 1 having the formula
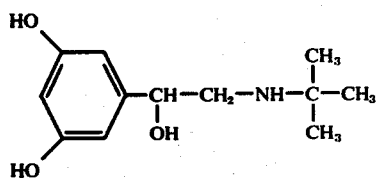
and pharmaceutically acceptable salts thereof.
3. The compound according to claim 1 having the formula
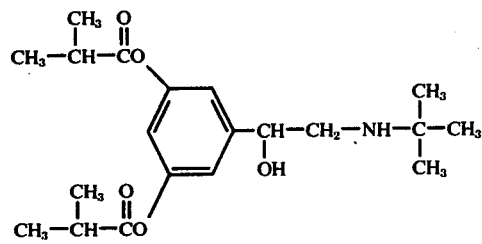
* * * * *